(12) United States Patent
Holloway et al.

(10) Patent No.: US 11,965,269 B2
(45) Date of Patent: Apr. 23, 2024

(54) MANUFACTURING GRADIENT MATERIALS USING MAGNETICALLY-ASSISTED ELECTROSPINNING

(71) Applicants: Julianne Holloway, Scottsdale, AZ (US); Kevin Tindell, Tempe, AZ (US)

(72) Inventors: Julianne Holloway, Scottsdale, AZ (US); Kevin Tindell, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 101 days.

(21) Appl. No.: 17/448,819

(22) Filed: Sep. 24, 2021

(65) Prior Publication Data
US 2022/0002908 A1 Jan. 6, 2022

Related U.S. Application Data

(62) Division of application No. 16/159,359, filed on Oct. 12, 2018, now abandoned.
(Continued)

(51) Int. Cl.
| | |
|---|---|
| *D01D 5/00* | (2006.01) |
| *A61L 27/04* | (2006.01) |
| *A61L 27/44* | (2006.01) |
| *A61L 27/48* | (2006.01) |
| *D01F 1/10* | (2006.01) |
| *D04H 3/015* | (2012.01) |

(Continued)

(52) U.S. Cl.
CPC ............ *D01D 5/0092* (2013.01); *A61L 27/04* (2013.01); *A61L 27/446* (2013.01); *A61L 27/48* (2013.01); *D01D 5/0015* (2013.01); *D01D 5/0069* (2013.01); *D01D 5/0076* (2013.01); *D01F 1/10* (2013.01); *D04H 3/015* (2013.01); *D04H 3/016* (2013.01); *D04H 3/04* (2013.01); *A61L 27/54* (2013.01); *A61L 2300/44* (2013.01); *A61L 2300/624* (2013.01); *A61L 2400/12* (2013.01); *A61L 2430/02* (2013.01); *A61L 2430/06* (2013.01); *B29C 70/16* (2013.01)

(58) Field of Classification Search
None
See application file for complete search history.

(56) References Cited

U.S. PATENT DOCUMENTS

| | | |
|---|---|---|
| 5,543,158 A | 8/1996 | Gref et al. |
| 5,578,325 A | 11/1996 | Domb et al. |

(Continued)

FOREIGN PATENT DOCUMENTS

| | | | | |
|---|---|---|---|---|
| WO | WO-2013181559 A1 | * | 12/2013 | ......... C01B 31/0206 |

OTHER PUBLICATIONS

Agarwal S, Wendorff JH, Greiner A. Use of electrospinning technique for biomedical applications. Polymer. 2008;49(26):5603-5621.

(Continued)

*Primary Examiner* — Emmanuel S Luk
(74) *Attorney, Agent, or Firm* — Michael Best & Friedrich LLP

(57) ABSTRACT

Described are fibrous materials comprising a plurality of fibers having a longitudinal alignment gradient and/or a longitudinal composition gradient. Also described are methods of preparing the fibrous materials thereof and methods of treating organ or tissue damage with the fibrous materials.

9 Claims, 24 Drawing Sheets

Specification includes a Sequence Listing.

Related U.S. Application Data

(60) Provisional application No. 62/571,730, filed on Oct. 12, 2017.

(51) Int. Cl.
    *D04H 3/016*      (2012.01)
    *D04H 3/04*      (2012.01)
    *A61L 27/54*      (2006.01)
    *B29C 70/16*      (2006.01)

(56) References Cited

U.S. PATENT DOCUMENTS

| | | | |
|---|---|---|---|
| 6,045,925 | A | 4/2000 | Klabunde et al. |
| 6,676,729 | B2 | 1/2004 | Sun |
| 6,878,445 | B2 | 4/2005 | Hattori et al. |
| 7,429,339 | B2 | 9/2008 | Renaud et al. |
| 7,459,145 | B2 | 12/2008 | Bao et al. |
| 7,462,446 | B2 | 12/2008 | Zhang et al. |
| 7,691,285 | B2 | 4/2010 | Teller et al. |
| 7,700,193 | B2 | 4/2010 | Chen et al. |
| 8,557,607 | B2 | 10/2013 | Penades et al. |
| 10,640,888 | B1 * | 5/2020 | Haff ................... D01D 5/0084 |
| 10,653,817 | B2 * | 5/2020 | Francis ................ D06N 3/0043 |
| 2005/0025971 | A1 | 2/2005 | Cho et al. |
| 2005/0201941 | A1 | 9/2005 | Cho et al. |
| 2007/0264199 | A1 | 11/2007 | Labhasetwar et al. |
| 2009/0108503 | A1 * | 4/2009 | Scott-Carnell ....... D01D 5/0084 |
| | | | 425/174.8 E |
| 2010/0233115 | A1 * | 9/2010 | Patel ....................... A61L 27/54 |
| | | | 425/174.8 E |
| 2015/0073551 | A1 * | 3/2015 | Uehlin ................... A61K 35/28 |
| | | | 623/13.12 |
| 2018/0106795 | A1 * | 4/2018 | Rajasekaran ......... B01J 19/0046 |
| 2019/0112731 | A1 * | 4/2019 | Holloway ............. D01D 5/0076 |
| 2019/0216979 | A1 * | 7/2019 | De Laporte ........... A61L 27/042 |
| 2019/0350688 | A1 * | 11/2019 | Hurtado .............. D06M 16/003 |
| 2021/0198792 | A1 * | 7/2021 | Wei ............................ C25B 1/02 |
| 2022/0195646 | A1 * | 6/2022 | Sota ................... D04H 1/43838 |
| 2022/0262578 | A1 * | 8/2022 | Wei ......................... H01G 11/32 |

OTHER PUBLICATIONS

Ajao, J. et al., "Electric-magnetic field-induced aligned electrospunpoly (ethylene oxide) (PEO) nanofibers", Journal of Materials Science, May 2010 [available online Jan. 2010], vol. 45, No. 9, pp. 2324-2329 <DOI:10.1007/s10853-009-4196-y>.

Baker BM, Mauck RL. The effect of nanofiber alignment on the maturation of engineered meniscus constructs. Biomaterials. 2007;28(11):1967-77.

Baker BM, Shah RP, Silverstein AM, Esterhai JL, Burdick JA, Mauck RL. Sacrificial nanofibrous composites provide instruction without impediment and enable functional tissue formation. Proceedings of the National Academy of Sciences. 2012;109(35):14176-81.

Baker, B. et al., "Fabrication and Modeling of Dynamic Multipolymer Nanofibrous Scaffolds", Journal of Biomechanical Engineering, Oct. 2009 [available online Sep. 2009], vol. 131, article 101012 <DOI:10.1115/1.3192140>.

Bashur CA, Shaffer RD, Dahlgren LA, Guelcher SA, Goldstein AS. Effect of fiber diameter and alignment of electrospun polyurethane meshes on mesenchymal progenitor cells. Tissue Engineering Part A. 2009;15(9):2435-45.

Bauer TW, Muschler GF., "Bone graft materials," Clinical Orthopaedics and Related Research. 2000; 371: 10-27.

Beason DP, Connizzo BK, Dourte LM, et al. Fiber-aligned polymer scaffolds for rotator cuff repair in a rat model. Journal of Shoulder and Elbow Surgery. 2012;21(2):245-250.

Boda SK, Almoshari Y, Wang H, et al. Mineralized nanofiber segments coupled with calcium-binding BMP-2 peptides for alveolar bone regeneration. Acta Biomaterialia.

Burdick JA, Prestwich GD. Hyaluronic acid hydrogels for biomedical applications. Adv Mater. 2011; 23:H41-56.

Caliari SR, Weisgerber DW, Grier WK, Mahmassani Z, Boppart MD, Harley BAC. Collagen Scaffolds Incorporating Coincident Gradations of Instructive Structural and Biochemical Cues for Osteotendinous Junction Engineering. Advanced Healthcare Materials.

Caplan AI. Adult mesenchymal stem cells for tissue engineering versus regenerative medicine. Journal of cellular physiology. 2007;213(2):341-7.

Carragee EJ, Hurwitz EL, Weiner BK., "A critical review of recombinant human bone morphogenetic protein-2 trials in spinal surgery: emerging safety concerns and lessons learned," The Spine Journal. 2011; 11: 471-91.

Chen ZX, Chang M, Peng YL, Zhao L, Zhan YR, Wang LJ, Wang R. Osteogenic growth peptide C-terminal pentapeptide [OGP (10-14)] acts on rat bone marrow mesenchymal stem cells to promote differentiation to osteoblasts and to inhibit differentiation to adipocytes. Regulatory peptides. 2007;142(1):16-23.

Chen, M. et al., "Electrically conductive nanofibers with highly oriented structures and their potential application in skeletal muscle tissue engineering", Acta Biomaterialia, Mar. 2013 [available online Oct. 2012], vol. 9 , No. 3, pp. 5562-5572 <DOI:10.1016/j.actbio.2012.10.024>.

Chi, W. et al., "Processing-Microstructure-Property Relations in Anisotropic Thermal Sprayed Composites", Materials Research Society, Symposium Proceedings, vol. 977, 2007, 0977-FF04-15.

Cook J., "The Current Status of Treatment for Large Meniscal Defects," Clinical Orthopaedics and Related Research., 2005; 435: 88-95.

Cottrell JM, Scholten P, Wanich T, Warren RF, Wright TM, Maher SA., "A new technique to measure the dynamic contact pressures on the Tibial Plateau," Journal of Biomechanics. 2008; 41: 2324-9.

Derwin KA, Badylak SF, Steinmann SP, Iannotti JP. Extracellular matrix scaffold devices for rotator cuff repair. Journal of Shoulder and Elbow Surgery. 2010;19(3):467-476.

Deutsch H., "High-dose bone morphogenetic protein-induced ectopic abdomen bone growth," The Spine Journal. 2010; 10: e1-4.

Dhandayuthapani B, Yoshida Y, Maekawa T, Kumar DS. Polymeric Scaffolds in Tissue Engineering Application: A Review. International Journal of Polymer Science. 2011;2011(5110):1-19.

Dominici ML, Le Blanc K, Mueller I, Slaper-Cortenbach I, Marini FC, Krause DS, Deans RJ, Keating A, Prockop DJ, Horwitz EM. Minimal criteria for defining multipotent mesenchymal stromal cells. The International Society for Cellular Therapy position statement. Cytotherapy. 2006;8(4):315-7.

Epstein NE., "Pros, cons, and costs of INFUSE in spinal surgery," Surgical Neurology International. 2011; 2: 10.

Font Tellado S, Balmayor ER, Van Griensven M. Strategies to engineer tendon/ligament-to-bone interface: Biomaterials, cells and growth factors. Advanced Drug Delivery Reviews. 2015;94:126-140.

Freeman S, Eddy SL, McDonough M, Smith MK, Okoroafor N, Jordt H, Wenderoth MP. Active learning increases student performance in science, engineering, and mathematics. Proceedings of the National Academy of Sciences. 2014;111(23):8410-5.

Fujihara, K., Kumar, A., Jose, R., Ramakrishna, S., & Uchida, S. (2007). Spray deposition of electrospun TiO2 nanorods for dye-sensitized solar cell. Nanotechnology, 18(36), 365709.

Gomez-Guillen MC, Gimenez B, Lopez-Caballero ME, Montero MP. Functional and bioactive properties of collagen and gelatin from alternative sources: A review. Food hydrocolloids. 2011;25(8):1813-1827.

Gordeuk, Vet al., "Carbonyl iron therapy for iron deficiency anemia" Blood, 1986. 67 (3): 745-752.

Gramlich WM, Kim IL, Burdick JA. Synthesis and orthogonal photopatterning of hyaluronic acid hydrogels with thiol-norbornene chemistry. Biomaterials. 2013;34(38):9803-11.

Gray, L. et al., "Green's Functions and Boundary Integral Analysis for Exponentially Graded Materials: Heat Conduction", Journal of Applied Mechanics, Jul. 2003, vol. 70, No. 4, pp. 543-549 <DOI:10.1115/1.1485753>.

(56) References Cited

OTHER PUBLICATIONS

Greene T, Lin C-C. Modular Cross-Linking of Gelatin-Based Thiol-Norbornene Hydrogels for in Vitro 3D Culture of Hepatocellular Carcinoma Cells. ACS Biomater Sci Eng.
Grier WK, Moy AS, Harley BAC. Cyclic tensile strain enhances human mesenchymal stem cell Smad 2/3 activation and tenogenic differentiation in anisotropic collagen-glycosaminoglycan scaffolds. eCM. 2017;33:227-239.
Guler, M. et al., "Contact Mechanics of FGM Coatings", in Golam, G., "Adaptive Structures, Eighth Japan/US Conference Proceedings" (CRC Press, Sep. 1998), pp. 397-406.
Heinlein B, Kutzner I, Graichen F, Bender A, Rohlmann A, Halder AM, et al., "ESB clinical biomechanics award 2008: Complete data of total knee replacement loading for level walking and stair climbing measured in vivo with a follow-up of 6-10 months," Clinical Biomechanics. 2009; 24: 315-26.
Highley CB, Prestwich GD, Burdick JA. Recent advances in hyaluronic acid hydrogels for biomedical applications. Current opinion in biotechnology. 2016;40:35-40.
Holloway JL, Lowman AM, Palmese GR. Mechanical evaluation of poly (vinyl alcohol)-based fibrous composites as biomaterials for meniscal tissue replacement. Acta biomaterialia. 2010;6(12):4716-24.
Holloway JL, Lowman AM, Palmese GR. The role of crystallization and phase separation in the formation of physically cross-linked PVA hydrogels. Soft Matter. 2013;9(3):826-33.
Holloway JL, Ma H, Rai R, Burdick JA., "Modulating hydrogel crosslink density and degradation to control bone morphogenetic protein delivery and in vivo bone formation," Journal of Controlled Release. 2014; 191: 63-70.
Holloway JL., "Development and Characterization of UHMWPE Fiber-Reinforced Hydrogels For Meniscal Replacement," Ph.D. Thesis, Drexel University. 2012.
Hosenpud JD, Bennett LE, Keck BM, Boucek MM, Novick RJ. The Registry of the International Society for Heart and Lung Transplantation: eighteenth official report—2001. The Journal of heart and lung transplantation. 2001;20(8):805-15.
Hosogane N, Huang Z, Rawlins BA, Liu X, Boachie-Adjei O, Boskey AL, et al., "Stromal derived factor-1 regulates bone morphogenetic protein 2-induced osteogenic differentiation of primary mesenchymal stem cells," The International Journal of Biochemistry & Cell Biology. 2010; 42:1132-41.
Hsu WK, Wang JC., "The use of bone morphogenetic protein in spine fusion," The Spine Journal. 2008; 8: 419-25.
Hu, Hao & Jiang, Wen & Lan, Fang & Zeng, Xiaobo & Ma, Shaohua & wu, Yao & Gu, Zhongwei. (2012). Synergic effect of magnetic nanoparticles on the electrospun aligned superparamagnetic nanofibers as a potential tissue engineering scaffold. RSC Adv 3. 879-886.
Huang C, Soenen SJ, Rejman J, Lucas B, Braeckmans K, Demeester J, De Smedt SC. Stimuli-responsive electrospun fibers and their applications. Chemical Society Reviews. 2011;40(5):2417-34.
Huang Z-M, Zhang YZ, Ramakrishna S, Lim CT. Electrospinning and mechanical characterization of gelatin nanofibers. Polymer. 2004;45(15):5361-5368.
Huang, C. et al., "Magnetic Electrospun Fibers for Cancer Therapy", Advanced Functional Materials, Jun. 2012 [available online Mar. 2012], vol. 22, No. 12, pp. 2479-2486 <DOI:10.1002/adfm.201102171>.
Hubbell JA. Biomaterials in Tissue Engineering. Nat Biotechnol. 1995;13(6):565-576.
Jiankang He, Ting Qin, Yaxiong Liu, Xiang Li, Dichen Li, Zhongmin Jin, Electrospinning of nanofibrous scaffolds with continuous structure and material gradients, Materials Letters, vol. 137, 2014, pp. 393-397.
Kai D, Liow SS, Loh XJ. Biodegradable polymers for electrospinning: towards biomedical applications. Materials Science and Engineering: C. 2014;45:659-70.

Khorshidi S, Solouk A, Mirzadeh H, et al. A review of key challenges of electrospun scaffolds for tissue-engineering applications. J Tissue Eng Regen Med. 2015;10(9):715-738.
Kim IL, Khetan S, Baker BM, Chen CS, Burdick JA. Fibrous hyaluronic acid hydrogels that direct MSC chondrogenesis through mechanical and adhesive cues. Biomaterials. 2013;34(22):5571-80.
Kim K-A, Zhao J, Andarmani S, Kakitani M, Oshima T, Binnerts ME, et al., "R-Spondin Proteins: A Novel Link to &beta ;-catenin Activation," Cell Cycle. 2006; 5: 23-6.
Kim M-J, Lee B, Yang K, et al. BMP-2 peptide-functionalized nanopatterned substrates for enhanced osteogenic differentiation of human mesenchymal stem cells. Biomaterials. 2013;34(30):7236-7246.
Kishan AP, Robbins AB, Mohiuddin SF, Jiang M, Moreno MR, Cosgriff-Hernandez EM. Fabrication of macromolecular gradients in aligned fiber scaffolds using a combination of in-line blending and air-gap electrospinning. Acta Biomaterialia, 2017, 56:118-128.
Kumar, V. et al., "Giant magnetoresistance of Fe3O4-polymethylmethacrylate nanocomposite aligned fibers via electrospinning ", Journal of Applied Physics, Jun. 2007, vol. 101, No. 11, article 114317 <DOI:10.1063/1.2745197>.
Kutzner I, Heinlein B, Graichen F, Bender A, Rohlmann A, Halder AM, et al., "Loading of the knee joint during activities of daily living measured in vivo in five subjects," Journal of Biomechanics. 2010; 43: 2164-73.
L Rossetti, et al., "The microstructure and micromechanics of the tendon-bone insertion," Nature Materials. 16(6): 2017.
Ladd MR, Lee SJ, Stitzel JD, Atala A, Yoo JJ. Co-electrospun dual scaffolding system with potential for muscle-tendon junction tissue engineering. Biomaterials. 2011;32(6):1549-59.
Langer R, Vacanti JP., "Tissue Engineering," Science. 1993; 260: 920-6.
Lawrence RC, Felson DT, Helmick CG, Arnold LM, Choi H, Deyo RA, et al., "Estimates of the Prevalence of Arthritis and Other Rheumatic Conditions in the United States, Part II," Arthritis and Rheumatism. 2008; 58: 26-35.
Lebaschi A, Deng X-H, Zong J, et al. Animal models for rotator cuff repair. Sun HB, ed. Annals of the New York Academy of Sciences. 2016;1383(1):43-57.
Leucht P, Minear S, Ten Berge D, Nusse R, Helms JA., "Translating insights from development into regenerative medicine: The function of Wnts in bone biology," Seminars in Cell & Developmental Biology.2008; 19: 434-43.
Li X, Xie J, Lipner J, Yuan X, Thomopoulos S, Xia Y. Nanofiber scaffolds with gradations in mineral content for mimicking the tendon-to-bone insertion site. Nano letters. 2009;9(7):2763-8.
Li Y, Huang G, Zhang X, Li B, Chen Y, Lu T, Lu TJ, Xu F. Magnetic hydrogels and their potential biomedical applications. Advanced Functional Materials. 2013;23(6):660-72.
Li, W. J., Mauck, R. L., Cooper, J. A., Yuan, X., & Tuan, R. S. (2007). Engineering controllable anisotropy in electrospun biodegradable nanofibrous scaffolds for musculoskeletal tissue engineering. Journal of biomechanics, 40(8), 1686-1693.
Liu, W. et al., "Fabrication of functionally graded TiC/Ti composites by Laser Engineered Net Shaping", Scripta Materialia, May 2003 [available online Feb. 2003], vol. 48, No. 9, pp. 1337-1342 <DOI:10.1016/S1359-6462(03)00020-4>.
Liu, Y. et al., "Magnetic-Field-Assisted Electrospinning of Aligned Straight and Wavy Polymeric Nanofibers", Advanced Materials, Jun. 2010, vol. 22, No. 22, pp. 2454-2457 <DOI:10.1002/adma.200903870>.
Logothetis CJ, Lin S-H., "Osteoblasts in Prostate Cancer Metastasis to Bone," Nature Reviews: Cancer. 2005; 5: 21-8.
Lohmander LS, Englund PM, Dahl LL, Roos EM., "The Long-term Consequence of Anterior Cruciate Ligament and Meniscus Injuries," The American Journal of Sports Medicine. 2007; 35:1756-69.
Lu HH, Jiang J., "Interface Tissue Engineering and the Formulation of Multiple-Tissue Systems," Advances in Biochemical Engineering/Biotechnology. 2006; 102: 91-111.
Lu HH, Subramony SD, Boushell MK, Zhang X. Tissue engineering strategies for the regeneration of orthopedic interfaces. Annals of biomedical engineering. 2010;38(6):2142-54.

(56) References Cited

OTHER PUBLICATIONS

Lutolf MP, Lauer-Fields JL, Schmoekel HG, Metters AT, Weber FE, Fields GB, et al., "Synthetic matrix metalloproteinase-sensitive hydrogels for the conduction of tissue regeneration: Engineering cell-invasion characteristics," Proceedings of the National Academy of Sciences. 2003; 100: 5413-8.

Ma Y, Zheng J, Amond EF, Stafford CM, Becker ML. Facile fabrication of "dual click" one-and two-dimensional orthogonal peptide concentration gradients. Biomacromolecules. 2013;14(3):665-71.

Makris EA, Hadidi P, Athanasiou KA., "The knee meniscus: Structureefunction, pathophysiology, current repair techniques, and prospects for regeneration," Biomaterials. 2011; 32: 7411-31.

Maletsky LP, Hillberry BM., "Simulating Dynamic Activities Using a Five-Axis Knee Simulator," Journal of Biomechanical Engineering. 2005; 127: 123-33.

Marklein RA, Burdick JA. Spatially controlled hydrogel mechanics to modulate stem cell interactions. Soft Matter. 2010;6(1):136-43.

Marklein RA, Lo Surdo JL, Bellayr IH, Godil SA, Puri RK, Bauer SR. High content imaging of early morphological signatures predicts long term mineralization capacity of human mesenchymal stem cells upon osteogenic induction. Stem cells. 2016;34(4):935-47.

McElvany MD, McGoldrick E, Gee AO, Neradilek MB, Matsen FA III. Rotator Cuff Repair. Am J Sports Med. 2015;43(2):491-500.

Moffat KL, Wang I-NE, Rodeo SA, Lu HH. Orthopedic interface tissue engineering for the biological fixation of soft tissue grafts. Clin Sports Med. 2009;28(1):157-176.

Moore NM, Lin NJ, Gallant ND, Becker ML. The use of immobilized osteogenic growth peptide on gradient substrates synthesized via click chemistry to enhance MC3T3-E1 osteoblast proliferation. Biomaterials. 2010;31(7):1604-11.

Mozdzen LC, Vucetic A, Harley BA. Modifying the strength and strain concentration profile within collagen scaffolds using customizable arrays of poly-lactic acid fibers. Journal of the mechanical behavior of biomedical materials. 2017;66:28-36.

Murphy MB, Hartgerink JD, Goepferich A, Mikos AG. Synthesis and in Vitro Hydroxyapatite Binding of Peptides Conjugated to Calcium-Binding Moieties. Biomacromolecules. 2007 ;8(7):2237-224 3.

National Science Foundation. NSF Strategic Plan for 2014-2018. 2014. [Report] Retrieved: https://www.nsf.gov/pubs/2014/nsf14043/nsf14043.pdf (Jul. 20, 2017).

Nerem RM, Sambanis A. Tissue Engineering: From Biology to Biological Substitutes. Tissue Engineering. 1995;1(1):3-13.

Nerurkar NL, Elliott DM, Mauck RL. Mechanics of oriented electrospun nanofibrous scaffolds for annulus fibrosus tissue engineering. Journal of orthopaedic research. 2007;25(8):1018-28.

Nuvoli, D. et al., "Synthesis and Characterization of Functionally Gradient Materials Obtained by Frontal Polymerization", ACS Applied Materials & Interfaces, Jan. 2015, vol. 7, No. 6, pp. 3600-3606 <DOI:10.1021/am507725k>.

O Ohtani, et al., "Collagen Fibrillar Networks as Skeletal Frameworks: A Demonstration by Cell-Maceration/Scanning Electron Microscope Method," Archives of Histology and Cytology. 51(3):1988.

O'Keefe RJ, Mao J., "Bone Tissue Engineering and Regeneration: From Discovery to the Clinic—An Overview," Tissue Engineering Part B, Reviews. 2011; 17:389-92.

P Ciampi, et al., "The Benefit of Synthetic Versus Biological Patch Augmentation in the Repair of Posterosuperior Massive Rotator Cuff Tears," The American Journal of Sports Medicine. 42(5): 2014.

Panyam J, Labhasetwar V., "Biodegradable nanoparticles for drug and gene delivery to cells and tissue," Advanced Drug Delivery Reviews. 2003; 55: 329-47.

Perera MM, Ayres N. Gelatin based dynamic hydrogels viathiol-norbornene reactions. Polym Chem. 2017;8(44):6741-6749.

Petri M, Warth RJ, Horan MP, Greenspoon JA, Millett PJ. Outcomes After Open Revision Repair of Massive Rotator Cuff Tears With Biologic Patch Augmentation. Arthroscopy: The Journal of Arthroscopic and Related Surgery. 2016;32(9):1752-1760.

Pew Research Center. Sharp Partisan Divisions in Views of National Institutions. 2017. [Report] Retrieved: http://www.people-press.org/2017/07/10/sharp-partisan-divisions-in-views-of-national-institutions/ (Jul. 20, 2017).

Pew Research Center. US public trust in science and scientists. 2017. [Report] Retrieved: https://www.slideshare.net/PewResearchCenter/us-public-trust-in-science-and-scientists (Jul. 20, 2017).

Piras AM, Chiellini F, Chiellini E, Nikkola L, Ashammakhi N. New multicomponent bioerodible electrospun nanofibers for dual-controlled drug release. Journal of Bioactive and Compatible Polymers. 2008;23(5):423-43.

Powell MC, Colin M. Meaningful citizen engagement in science and technology: What would it really take? Science Communication. 2008;30(1):126-36.

PP Provenzano, et al., "Collagen fibril morphology and organization: Implications for force transmission in ligament and tendon," Matrix Biology. 25(2): 2006.

Prince M. Does active learning work? A review of the research. Journal of engineering education. Jul. 1, 2004;93(3):223-31.

Purcell BP, Elser JA, Mu A, Margulies KB, Burdick JA. Synergistic effects of SDF-1α chemokine and hyaluronic acid release from degradable hydrogels on directing bone marrow derived cell homing to the myocardium. Biomaterials. 2012;33(31):7849-57.

Qin T-W, Sun Y-L, Thoreson AR, et al. Effect of mechanical stimulation on bone marrow stromal cell-seeded tendon slice constructs: A potential engineered tendon patch for rotator cuff repair. Biomaterials. 2015;51:43-50.

Rehmann MS, Luna JI, Maverakis E, Kloxin AM. Tuning microenvironment modulus and biochemical composition promotes human mesenchymal stem cell tenogenic differentiation. J Biomed Mater Res. 2016;104(5):1162-1174.

Robertson DB, Daniel DM, Biden E. Soft tissue fixation to bone. The American journal of sports medicine. 1986;14(5):398-403.

Rossetti L, Kuntz LA, Kunold E, et al. The microstructure and micromechanics of the tendon-bone insertion. Nat Mater. 2017;16(6):664-670.

Saadat F, Deymier AC, Birman V, Thomopoulos S, Genin GM. The concentration of stress at the rotator cuff tendon-to-bone attachment site is conserved across species. Journal of the mechanical behavior of biomedical materials. 2016;62:24-32.

Sahoo S, Chung C, Khetan S, Burdick JA. Hydrolytically degradable hyaluronic acid hydrogels with controlled temporal structures. Biomacromolecules. 2008;9(4):1088-92.

Sahoo S, Ouyang H, Goh JC, Tay TE, Toh SL. Characterization of a novel polymeric scaffold for potential application in tendon/ligament tissue engineering. Tissue engineering. 2006;12(1):91-9.

Sahoo S, Teh TK, He P, Toh SL, Goh JC., "Interface Tissue Engineering: Next Phase in Musculoskeletal Tissue Repair," Annals of the Academy of Medicine. 2011; 40:245-51.

Samavedi S, Horton CO, Guelcher SA, Goldstein AS, Whittington AR. Fabrication of a model continuously graded co-electrospun mesh for regeneration of the ligament-bone interface. Acta biomaterialia. 2011;7(12):4131-8.

Samavedi S, Vaidya P, Gaddam P, Whittington AR, Goldstein AS. Electrospun meshes possessing region-wise differences in fiber orientation, diameter, chemistry and mechanical properties for engineering bone-ligament-bone tissues. Biotechnol Bioeng. Dec. 2014; 111(12):2549-59.

Sano H, Yamashita T, Wakabayashi I, Itoi E. Stress distribution in the supraspinatus tendon after tendon repair. The American journal of sports medicine. 2007;35(4):542-6.

Santoro M, Tatara AM, Mikos AG. Gelatin carriers for drug and cell delivery in tissue engineering. Journal of Controlled Release. 2014;190(C):210-218.

Seeherman H, Wozney JM., "Delivery of bone morphogenetic proteins for orthopedic tissue regeneration," Cytokine & Growth Factor Reviews. 2005; 16: 329-45.

Shen, H., "Nonlinear bending of functionally graded carbon nanotube-reinforced composite plates in thermal environments", Composite Structures, Nov. 2009 [available online Apr. 2009], vol. 91, No. 1, pp. 9-19 <DOI:10.1016/j.compstruct.2009.04.026>.

(56) References Cited

OTHER PUBLICATIONS

Shi J, Wang L, Zhang F, Li H, Lei L, Liu L, Chen Y. Incorporating protein gradient into electrospun nanofibers as scaffolds for tissue engineering. ACS applied materials & interfaces. 2010;2(4):1025-30.

Shrivats AR, McDermott MC, Hollinger JO., "Bone tissue engineering: state of the union," Drug Discovery Today. 2014; 19: 781-6.

Silber JS, Anderson DG, Daffner SD, Brislin BT, Leland JM, Hilibrand AS, et al., "Donor Site Morbidity After Anterior Iliac Crest Bone Harvest for Single-Level Anterior Cervical Discectomy and Fusion," Spine. 2003; 28: 134-9.

Sill TJ, Recum von HA. Electrospinning: Applications in drug delivery and tissue engineering. Biomaterials. 2008;29(13):1989-2006.

Sommers MB, Fitzpatrick DC, Kahn KM, Marsh JL, Bottlang M., "Hinged External Fixation of the Knee Intrinsic Factors Influencing Passive Joint Motion," Journal of Orthopaedic Trauma. 2004; 18: 163-9.

Song, T. et al., "Encapsulation of self-assembled FePt magnetic nanoparticles in PCL nanofibers by coaxial electrospinning", Chemical Physics Letters, Nov. 2005 [Sep. 2005], vol. 415, No. 4-6, pp. 317-322 <DOI:10.1016/j.cplett.2005.09.035>.

Soslowsky LJ, Carpenter JE, DeBano CM, Banerji I, Moalli MR. Development and use of an animal model for investigations on rotator cuff disease. Journal of Shoulder and Elbow Surgery. 1996;5(5):383-392.

Stevens MM., "Biomaterials for bone tissue engineering," Materials Today. 2008; 11: 18-25.

Sun C, Lee JSH, Zhang M., "Magnetic nanoparticles in MR imaging and drug delivery," Advanced Drug Delivery Reviews. 2008; 60: 1252-65.

Sundararaghavan HG, Burdick JA. Gradients with depth in electrospun fibrous scaffolds for directed cell behavior. Biomacromolecules. 2011;12(6):2344-50.

Suresh, S., "Graded Materials for Resistance to Contact Deformation and Damage", Science, Jun. 2001, vol. 292, No. 5526, pp. 2447-2451, <DOI:10.1126/science.1059716 >.

Teh TKH, Toh S-L, Goh JCH. Aligned Fibrous Scaffolds for Enhanced Mechanoresponse and Tenogenesis of Mesenchymal Stem Cells. Tissue Engineering Part A. 2013; 19(11-12):1360-1372.

Tellado SF, Balmayor ER, Van Griensven M. Strategies to engineer tendon/ligament-to-bone interface: Biomaterials, cells and growth factors. Advanced drug delivery reviews. 2015;94:126-40.

Terenzini PT, Springer L, Yaeger PM, Pascarella ET, Nora A. First-generation college students: Characteristics, experiences, and cognitive development. Research in Higher education. 1996;37(1):1-22.

Thomopoulos S, Hattersley G, Rosen V, et al. The localized expression of extracellular matrix components in healing tendon insertion sites: an in situ hybridization study. J Orthop Res. 2002;20(3):454-463.

Thomopoulos S, Williams GR, Gimbel JA, Favata M, Soslowsky LJ. Variation of biomechanical, structural, and compositional properties along the tendon to bone insertion site. Journal of orthopaedic research. 2003;21(3):413-9.

Tous E, Ifkovits JL, Koomalsingh KJ, Shuto T, Soeda T, Kondo N, Gorman III JH, Gorman RC, Burdick JA. Influence of injectable hyaluronic acid hydrogel degradation behavior on infarction-induced ventricular remodeling. Biomacromolecules. 2011;12(11):4127-35.

Udupa, G. et al., "Functionally Graded Composite Materials: An Overview", Procedia Materials Science, Sep. 2014, vol. 5, pp. 1291-1299 <DOI:10.1016/j.mspro.2014.07.442>.

United States Census. https://www.census.gov/quickfacts/az. This website details Arizona census information, particularly the number of people in Arizona over the age of 65, available at least as early as Dec. 29, 2018.

US Food and Drug Administration. Challenge and Opportunity on the Critical Path to New Medical Products. 2004. <http://www.fda.gov/ScienceResearch/SpecialTopics/CriticalPathInitiative/CriticalPathOpportunitiesReports/ucm077262.htm> (Accessed: Dec. 9, 2014).

Wade RJ, Bassin EJ, Gramlich WM, Burdick JA. Nanofibrous hydrogels with spatially patterned biochemical signals to control cell behavior. Advanced Materials. 2015;27(8):1356-62.

Wang, H. et al., "Fabrication of aligned ferrite nanofibers by magnetic-field-assisted electrospinning coupled with oxygen plasma treatment", Materials Research Bulletin, Aug. 2009 [available online May 2009], vol. 44, No. 8, pp. 1676-1680 <DOI:10.1016/j.materresbull.2009.04.006>.

Wang, M. et al., "Field-responsive superparamagnetic composite nanofibers by electrospinning", Polymer, Jul. 2004, vol. 45, No. 16, pp. 5505-5514 <DOI:10.1016/j.polymer.2004.06.013>.

Xie J, Ma B, Michael PL, Shuler FD. Fabrication of nanofiber scaffolds with gradations in fiber organization and their potential applications. Macromol Biosci. Oct. 2012; 12(10): 1336-41.

Yang PJ, Temenoff JS., "Engineering Orthopedic Tissue Interfaces," Tissue Engineering Part B, Reviews. 2009; 15: 127-41.

Yang, D. et al., "Aligned electrospun nanofibers induced by magnetic field", Journal of Applied Polymer Science, Dec. 2008 [available online Sep. 2008], vol. 110, No. 6, pp. 3368-3372 <DOI:10.1002/app.28896>.

Yang, D. et al., "Fabrication of Aligned Fibrous Arrays by Magnetic Electrospinning", Advanced Materials, Nov. 2007, vol. 19, No. 21, pp. 3702-3706 <DOI: 10.1002/adma.200700171>.

Yin Z, Chen X, Chen JL, Shen WL, Nguyen TM, Gao L, Ouyang HW. The regulation of tendon stem cell differentiation by the alignment of nanofibers. Biomaterials. 2010;31(8):2163-75.

Yoo HS, Lee EA, Yoon JJ, Park TG. Hyaluronic acid modified biodegradable scaffolds for cartilage tissue engineering. Biomaterials. 2005; 26:1925-1933.

Zhang X, Bogdanowicz D, Erisken C, Lee NM, Lu HH. Biomimetic scaffold design for functional and integrative tendon repair. Journal of Shoulder and Elbow Surgery.

Zhang YZ, Venugopal J, Huang ZM, Lim CT, Ramakrishna S. Crosslinking of the electrospun gelatin nanofibers. Polymer. 2006;47(8):2911-2917.

Zong, X., Kim, K., Fang, D., Ran, S., Hsiao, B. S., & Chu, B. (2002). Structure and process relationship of electrospun bioabsorbable nanofiber membranes. Polymer, 43(16), 4403-4412.

Zuiker, J. et al., "The effective properties of functionally graded composites—I. Extension of the mori-tanaka method to linearly varying fields", Composites Engineering, 1994, vol. 4, No. 1, pp. 19-35 <DOI:10.1016/0961-9526(94)90004-3>.

\* cited by examiner

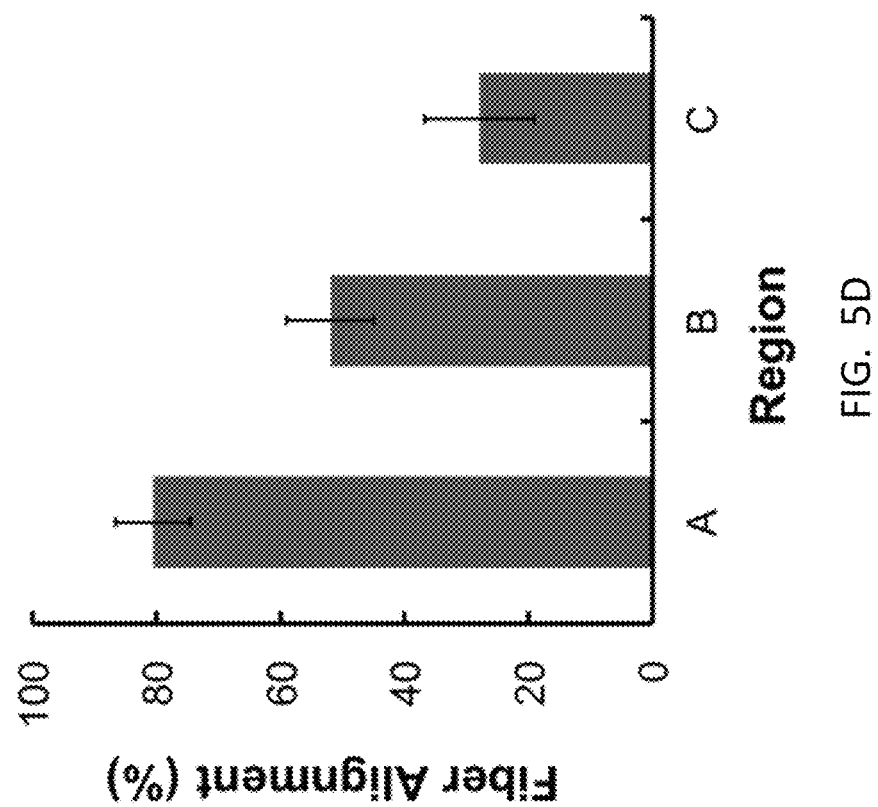
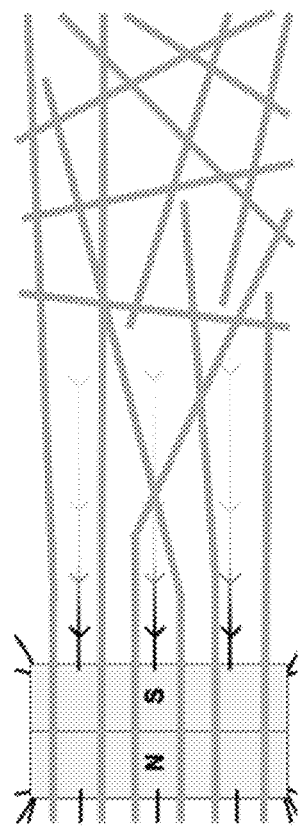
FIG. 5A
FIG. 5B
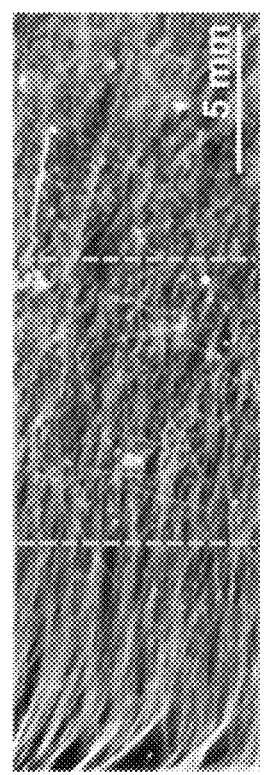
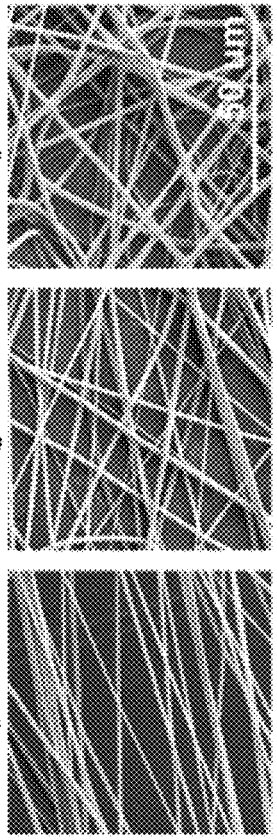
FIG. 5C

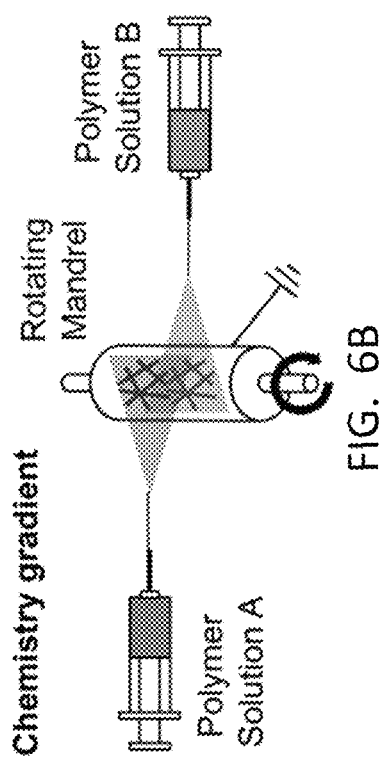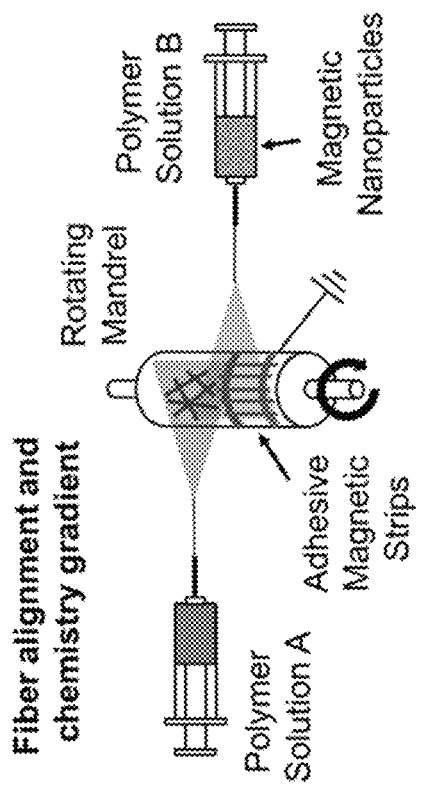

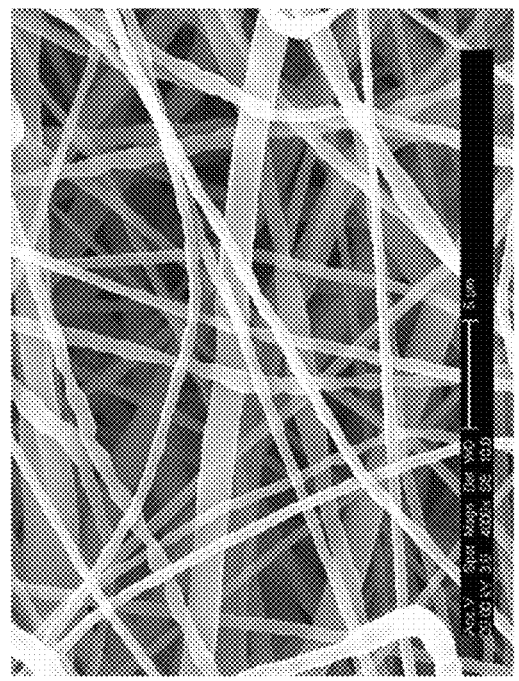
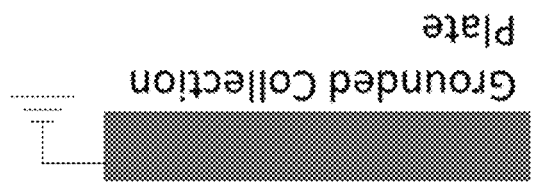
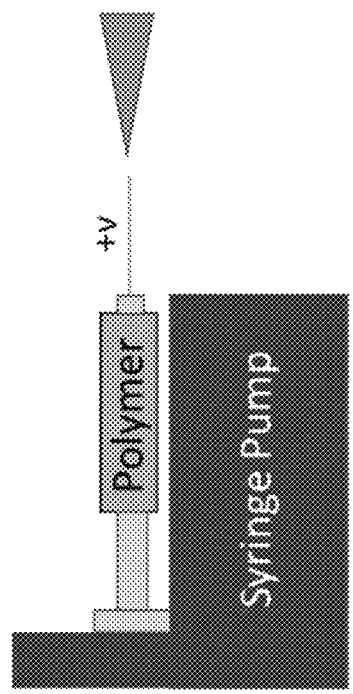
FIG. 7B
FIG. 7A

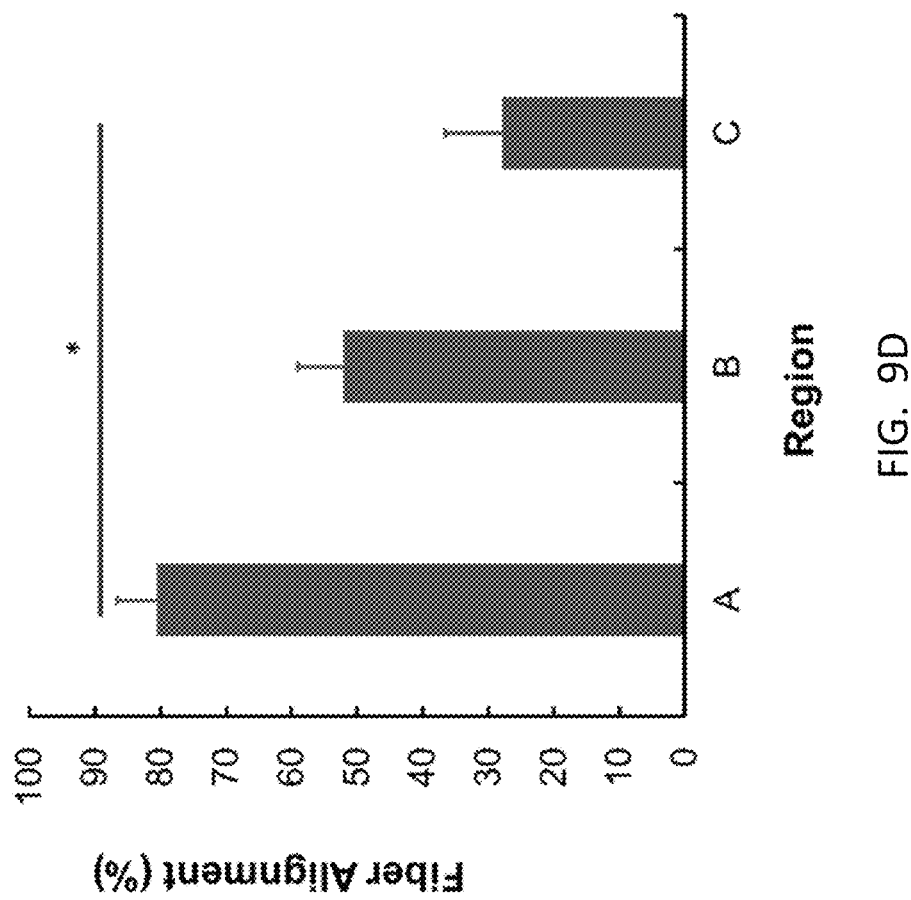
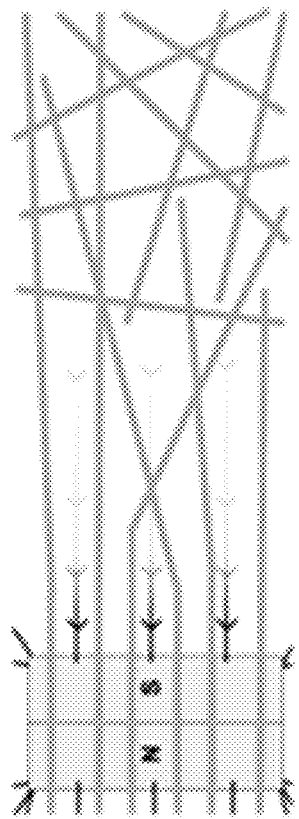
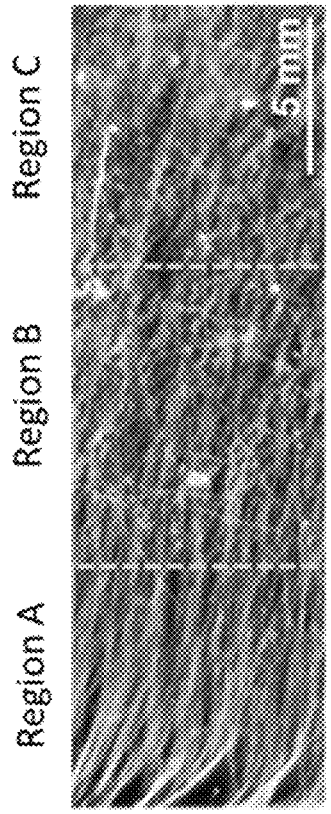
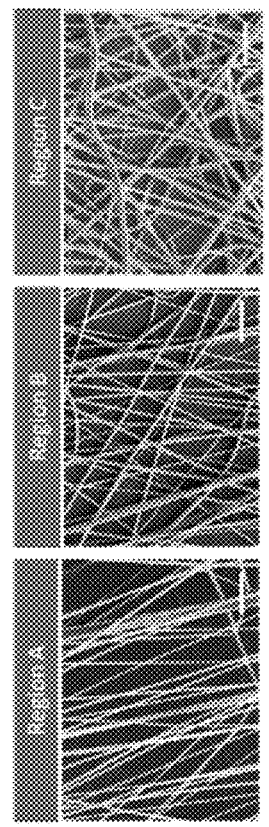
FIG. 9A
FIG. 9B
FIG. 9C
FIG. 9D

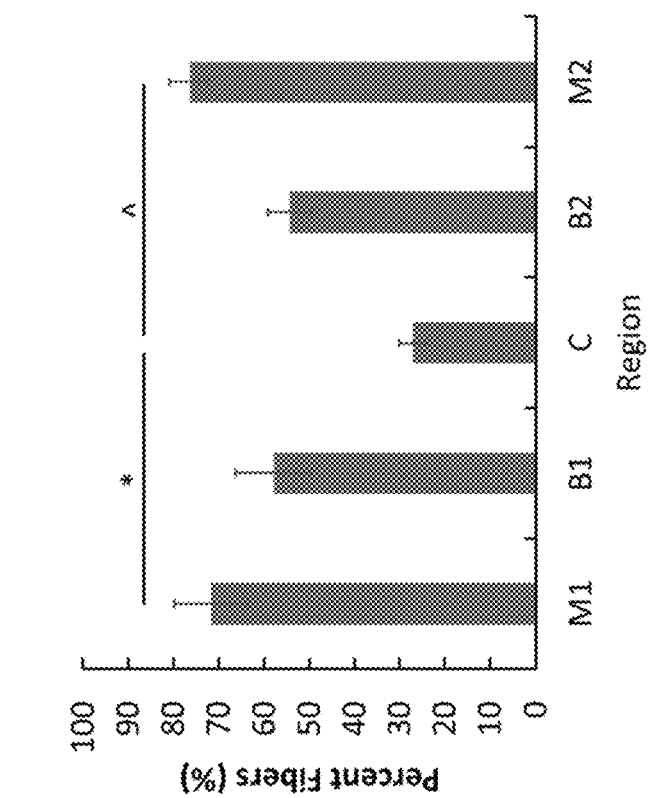
FIG. 13C
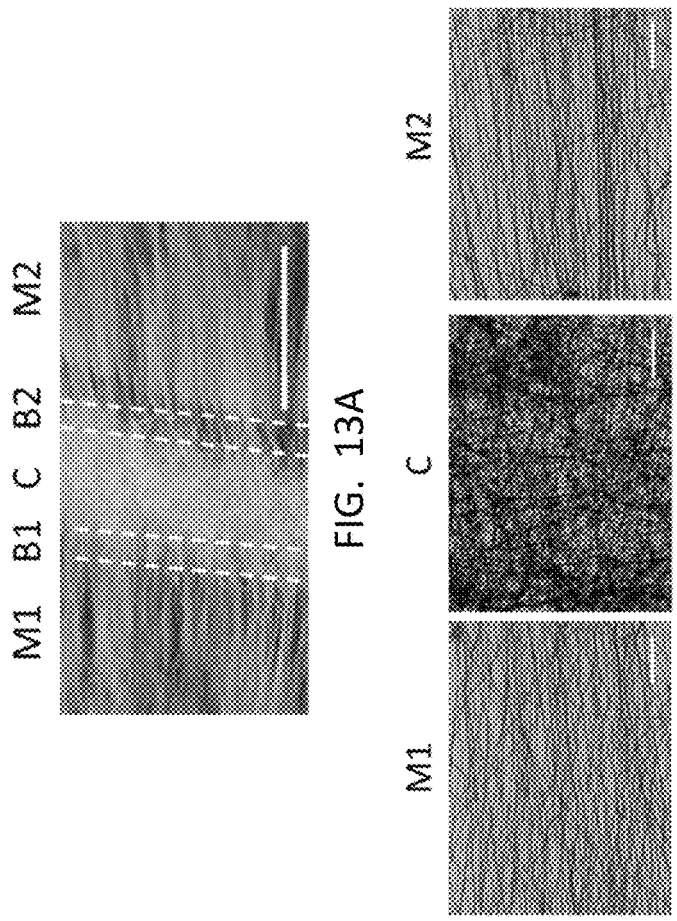
FIG. 13A
FIG. 13B

Scale = 1 cm (macroscopic), 150 μm (microscopic)

Scale = 1 cm (macroscopic), 150 μm (microscopic)

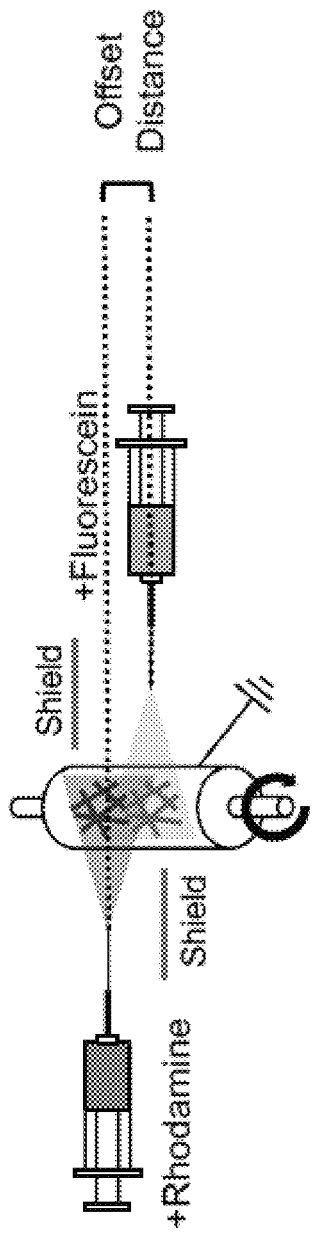
FIG. 18A
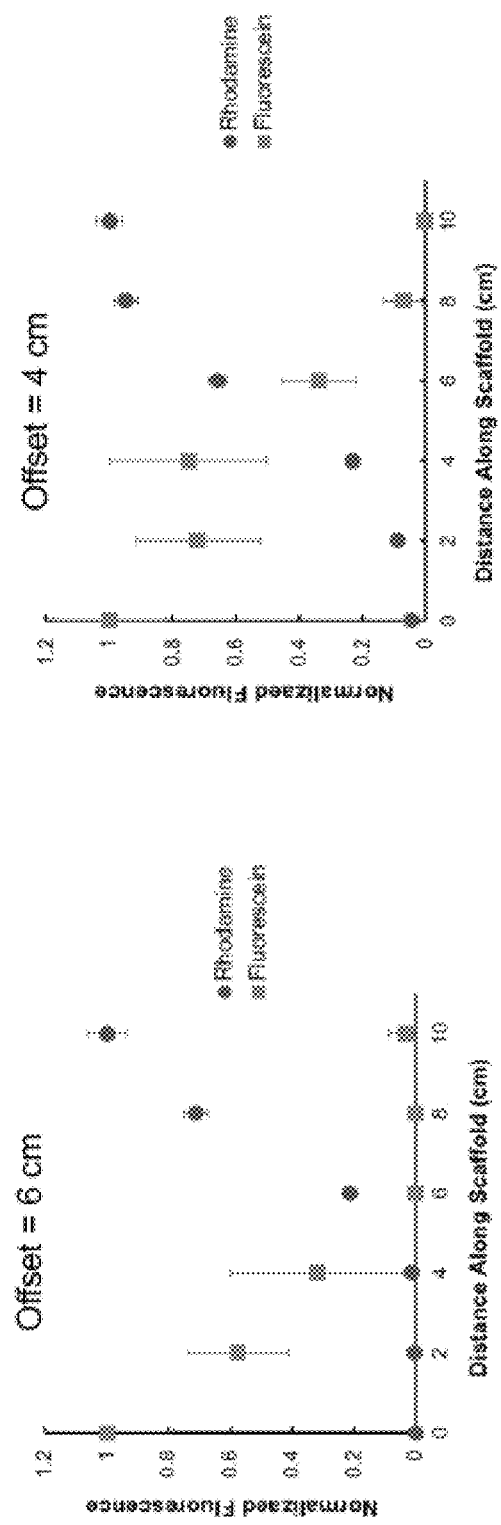
FIG. 18B
FIG. 18C

```
                    SEQUENCE LISTING

<160> NUMBER OF SEQ ID NOS: 3

<210> SEQ ID NO 1
<211> LENGTH: 11
<212> TYPE: PRT
<213> ORGANISM: Artificial sequence
<220> FEATURE:
<223> OTHER INFORMATION: Synthetic

<400> SEQUENCE: 1

Gly Cys Gly Tyr Gly Arg Gly Asp Ser Pro Gly
1               5                   10

<210> SEQ ID NO 2
<211> LENGTH: 16
<212> TYPE: PRT
<213> ORGANISM: Artificial sequence
<220> FEATURE:
<223> OTHER INFORMATION: Synthetic

<400> SEQUENCE: 2

Gly Cys Ala Leu Lys Arg Gln Gly Arg Thr Leu Tyr Gly Phe Gly Gly
1               5                   10                  15

<210> SEQ ID NO 3
<211> LENGTH: 16
<212> TYPE: PRT
<213> ORGANISM: Artificial sequence
<220> FEATURE:
<223> OTHER INFORMATION: Synthetic

<400> SEQUENCE: 3

Gly Cys Arg Asp Gly Pro Gln Gly Ile Trp Gly Gln Asp Arg Cys Gly
1               5                   10                  15
```

MANUFACTURING GRADIENT MATERIALS USING MAGNETICALLY-ASSISTED ELECTROSPINNING

CROSS REFERENCE TO RELATED APPLICATIONS

This application claims the benefit of U.S. Provisional Application No. 62/571,730, filed Oct. 12, 2017, which is incorporated herein by reference in their entirety.

SEQUENCE LISTING

The instant application contains a Sequence Listing which has been submitted electronically in ASCII format and is hereby incorporated by reference in its entirety. Said ASCII copy, created on Oct. 11, 2018, is named "208192-9046-US03_Sequence_Listing" and is 983 bytes in size.

TECHNICAL FIELD

The present disclosure relates to the field of electrospun fibrous material with gradients in fiber alignment and/or structure, as well as methods for making and using the electrospun fibrous materials.

BACKGROUND

Every year millions of patients suffer from organ or tissue damage as a result of trauma or disease. Surgical treatment options in the event of significant organ or tissue damage remain poor, where donor tissue transplantation (e.g., heart), autograft tissue transplantation (e.g., bone), or simple removal of the injured tissue (e.g., meniscus) remain the most common treatment options. To address the limitations associated with these treatment options, the field of tissue engineering seeks to regenerate the injured or diseased tissue through a combination of cells, material scaffolding, and signaling molecules. Although there have been significant advances within the field, translation has proven difficult with ongoing challenges regenerating complex tissues with a heterogeneous structure and multiple cell types. This can be attributed to a lack of biomaterials capable of mimicking the heterogeneous structures of many tissues that are responsible for tissue function and spatially controlling cellular behavior.

In particular, the transitional or interfacial tissue between distinct, adjacent tissues has complex gradients of structure, cell type, and chemical composition. As an example, a schematic of the types of gradients present in the tendon or ligament to bone interfacial tissue is shown in FIG. 1, where the tissue gradually transitions from highly aligned fibrous tissue to calcified bone. For transitions between musculoskeletal tissues (e.g., ligament or tendon to bone, muscle to tendon, cartilage to bone, etc.), the interfacial region is critical for transferring mechanical load from one tissue type to another. Due to the high stress concentrations that can occur at these interfaces during load transfer, interfacial tissue is also commonly identified as the failure location during associated injuries. Following injury, it is critical to regenerate the interfacial tissue in order to adequately restore function. Developing new biomaterial fabrication strategies capable of mimicking the heterogeneous nature of interfacial tissues, as well as other complex tissues, is vital for spatially controlling cellular behavior and resulting in functional heterogeneous tissue regeneration.

A majority of musculoskeletal tissue engineering research aimed to address these issues has focused on the regeneration or replacement of one particular tissue type (i.e., bone, cartilage, or ligament) and neglected to address the musculoskeletal tissue interfaces that serve as the connection between these tissues. Musculoskeletal tissue interfaces, such as muscle-tendon and ligament-bone interfaces, exhibit gradients in structure, chemical composition, and mechanics and are critical for effectively transferring stress from one tissue type to another. Most musculoskeletal repair surgeries fail to regenerate the complex interfacial tissue after injury which is likely a significant cause for poor mechanical performance and re-injury.

Although significant progress has been made in the understanding of how cells interact with their local environment; the majority of tissue engineering research utilizes homogeneous materials with isotropic mechanical properties. Fabricating biomaterials capable of replicating the heterogeneous structure and chemistry of multicellular, complex tissues remains a significant challenge within tissue engineering. Due to limitations in current fabrication methods, new techniques are needed to manufacture materials capable of replicating the natural heterogeneity of complex tissues. Specifically, new fabrication methods are desired that can create independent gradients in fiber alignment and chemistry similar to those present in interfacial tissues.

Electrospinning is a highly versatile fabrication method for producing scaffolds that mimic the fibrous nature of the extracellular matrix (ECM). During electrospinning, an electrical field is used to direct polymer fiber deposition onto a collector with typical fiber diameters less than 1 $\mu$m. The process of electrospinning positively charges a polymer solution, resulting in propulsion of the polymer towards a grounded or negatively charged collector (FIG. 7A). The solvents of the polymer solution evaporate during time of flight and the polymer is collected in the form of micro or nanofibers (FIG. 7B). Electrospun fibrous materials are desirable due to their small fiber size, high surface area, and ability to mimic the extracellular matrix of many tissues.

Furthermore, as shown in FIG. 2, a rotating collection mandrel can be used to induce fiber alignment and mimic the aligned fibrous nature of many musculoskeletal tissues (e.g., ligaments, tendons, meniscus, etc.) by rotating at high speeds (~7.5 m/s for >80% fiber alignment). Several electrospinning techniques have been utilized to fabricate gradient fibrous scaffolds, including: offset multicomponent electrospinning, changing electrospinning parameters with time, and post-electrospinning. In offset multicomponent electrospinning, two or more individual polymer jets are displaced along the axis of the collector resulting in gradients in fiber chemistry and/or mechanics along the length of the scaffold. Changing the electrospinning parameters during spinning can also create material gradients, including: increasing the mandrel rotation speed over time resulting in a gradient in fiber alignment and controllably adding a second solution to the primary electrospinning solution over time (also known as in-line blending) resulting in a gradient in fiber chemistry. Typically, during electrospinning, a scaffold is built over time by the deposition of sequential fiber layers. As a result, any changes in electrospinning parameters over time cause gradual changes to the layers being depositing and result in gradients along the thickness of the scaffold. Additionally, post-electrospinning steps can be performed to introduce chemical functionalization gradients or patterns along fibrous scaffolds, such as spatially controlled photoconjugation of cell-adhesive peptides.

None of the current electrospinning methods are capable of creating gradients in fiber alignment that mimic the natural heterogeneous fiber organization shown in FIG. 1, where the gradient in fiber alignment occurs along the length of the tissue or longitudinally. Replicating this gradient is critical, as fiber alignment is known to influence material mechanics; cellular alignment, gene expression, and differentiation; and new tissue organization. Electrospun fibrous scaffolds have been generated with longitudinal gradients in fiber alignment using air-gap electrospinning, where the organization of parallel copper wires on a rotating collector allows for some control over fiber alignment. Air-gap electrospinning can be combined with in-line blending to create gradients in fiber alignment and chemistry; however, the possible chemical gradients are limited due to the nature of in-line blending (e.g., the blending solution has to be miscible with the primary electrospinning solution).

There is a need for new tissue engineering constructs for regeneration of tissue at the musculoskeletal tissue interfaces that serve as the connection between the above-described tissues.

SUMMARY OF THE INVENTION

The present invention is directed to a fibrous material comprising a plurality of polymer fibers, wherein the plurality of fibers has a longitudinal alignment gradient of more than 70% aligned to less than 35% aligned.

The present invention is directed to a method of preparing said fibrous material comprising a plurality of polymer fibers. The method comprises: electrospinning a polymer fiber onto a collector having a first portion and a second portion to provide said fibrous material, wherein at least one portion of the collector comprises a magnetic field.

The present invention is directed to a fibrous material comprising a plurality of polymer fibers. The plurality of polymer fibers comprises: a first fiber; and optionally a second fiber, wherein the fibrous material has a longitudinal composition gradient and the plurality of fibers has a longitudinal alignment gradient.

The present invention is directed to a method of preparing said fibrous material comprising a plurality of polymer fibers. The method comprises: electrospinning a first fiber and optionally a second fiber onto a collector having a first portion and a second portion to provide said fibrous material, wherein at least one portion of the collector comprises a magnetic field.

The present invention is directed to a fibrous material comprising a plurality of fibers. The plurality of fibers includes: a first fiber; and a second fiber comprising a metal nanoparticle, wherein the plurality of fibers have a longitudinal composition gradient and a longitudinal alignment gradient.

The present invention is directed to a method of preparing said fibrous material comprising a plurality of fibers. The method comprises: electrospinning a first fiber and a second fiber comprising a metal nanoparticle onto a collector having a first portion and a second portion to provide said fibrous material, wherein at least one portion of the collector comprises at least one magnet.

The present invention is directed to a method of treating organ or tissue damage in a subject. The method comprises introducing said fibrous material into a subject in need thereof at or near the organ or tissue.

Other aspects of the invention will become apparent by consideration of the detailed description and accompanying drawings.

BRIEF DESCRIPTION OF THE DRAWINGS

FIGS. 5A-5D show fiber characteristics from magnetically-assisted electrospinning. Schematic showing magnetic field direction and resulting fiber alignment (FIG. 5A). Photo (FIG. 5B), SEM image (FIG. 5C), and fiber alignment (FIG. 5D) of single component fibrous scaffolds with gradients in fiber alignment.

FIGS. 6A-6C show dual-jet electrospinning. Dual-jet electrospinning system with rotating cylindrical mandrel. Proposed multicomponent, magnetically-assisted electrospinning technique (FIG. 6A). Offset polymer solutions allow for the formation of gradients in fiber chemistry (FIG. 6B) and selective magnetic field application allows for the formation of gradients in fiber alignment (FIG. 6C).

FIGS. 7A-7B show electrospinning on a grounded plate. Schematic of the electrospinning process of a positively charged polymer solution onto a grounded collection plate (FIG. 7A). Scanning electron microscopy image of the collected electrospun fibers (FIG. 7B).

FIGS. 9A-9D show fiber characteristics from magnetically-assisted electrospinning. Schematic (FIG. 9A) showing magnetic field direction (black) and resulting fiber alignment (green). Bright field (FIG. 9B, scale=5 mm) and SEM (FIG. 9C, scale=20 μm) images of electrospun fibers within each region, where region A was closest and region C was furthest from the magnet. Fiber alignment quantification (FIG. 9D) as a function of region indicating fiber alignment increases with increasing magnetic field strength. All fiber alignment regions were statistically significant ($p<0.05$).

FIGS. 13A-13C show alternating fiber alignment with magnets separated one cm. Macroscopic images (FIG. 13A, scale=1 cm), bright field microscopy (FIG. 13B scale=150 μm) images, and fiber alignment (FIG. 13C) quantification confirming fibers transition from aligned to unaligned to aligned between M1, C, and M2 regions, respectively. Regions are labeled as follows: M1 (magnet 1), B1 (transition region 1), C (center of two magnets), B2 (transition region 2) and M2 (magnet 2).

FIG. 15C shows cell morphology (scale=150 μm). FIG. 15D is a graph showing cell aspect ratio.

FIGS. 18A-18E show multi-component, offset electrospinning for creating a chemistry gradient. A schematic of the process used for offset electrospinning using two fiber components, where one component contains a rhodamine dye and the other contains a fluorescein dye (FIG. 18A). Normalized fluorescence of rhodamine and fluorescein as a function of distance along the length of the scaffold for a 6 cm offset configuration (FIG. 18B and FIG. 18D) and a 4 cm offset configuration (FIG. 18C and FIG. 18E).

DETAILED DESCRIPTION

Figure 1:
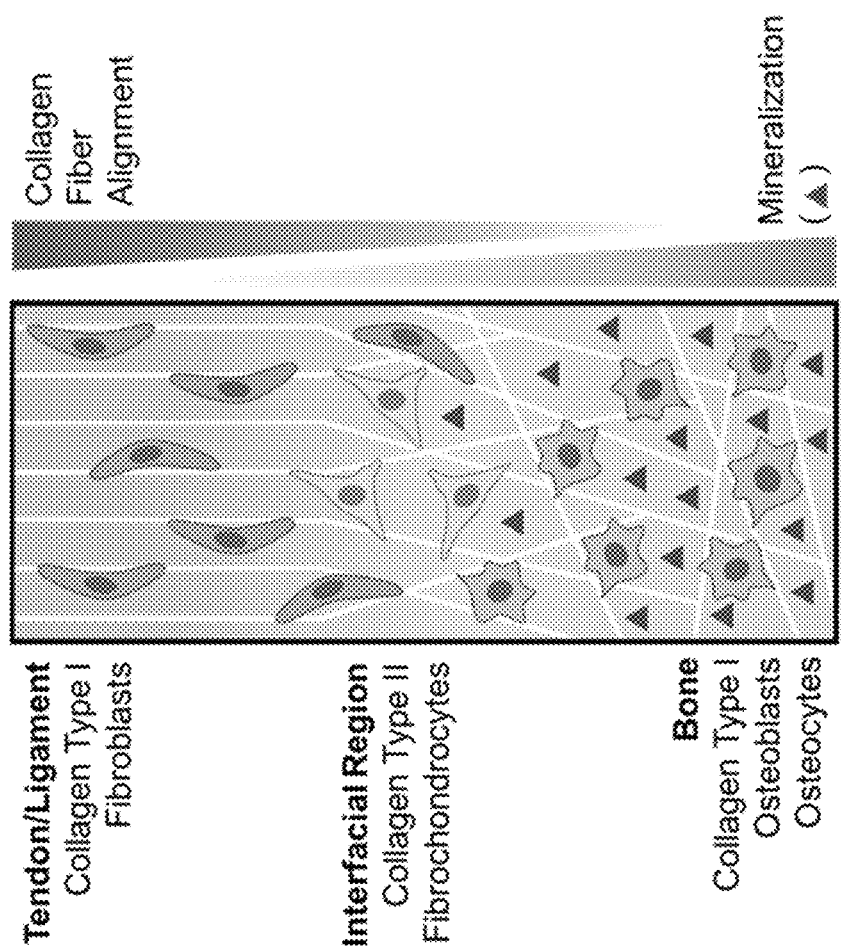
FIG. 1 shows a schematic detailing the heterogeneous nature of the tendon/ligament to bone interfacial tissue, with aligned collagen type I in the ligament/tendon compartment and unaligned mineralized tissue in the bone compartment.

The present disclosure describes electrospun fibrous materials that mimic the extracellular matrix of interfacial tissues through the manufacturing of structurally and chemically gradient fibrous materials using a novel magnetically-assisted electrospinning technique which may be combined with multicomponent (multi-jet) electrospinning. Magnetic electrospinning and the combination of magnetic electrospinning with multicomponent (multi-jet) electrospinning allow for the manufacture of novel electrospun fibrous materials with gradients in fiber alignment and structure.

The novel electrospinning technique is utilized to manufacture electrospun fibrous scaffolds with gradients in chemical and physical structure within the same layer of fiber deposition (along the length of the scaffold). Gradients are of particular interest due to their biological importance in effectively transferring stress between musculoskeletal tissues during movement, where natural physical and chemical gradients exist at the interface of most musculoskeletal tissues (e.g., ligament to bone, cartilage to bone, and muscle to tendon). Current electrospinning techniques are incapable of creating gradients in fiber alignment and chemistry within the same layer of fiber deposition (along the length of the scaffold) and are generally limited to creating gradients in thickness. This differentiation is important, as most interfacial tissues have gradients in structure along the same "layer" of fibrous tissue. The disclosed gradient fibrous materials can be used as tissue-engineered constructs for musculoskeletal interfacial tissue regeneration and repair. Broader impacts and uses may also be present for non-musculoskeletal tissue engineering where control over scaffold structure and composition is important.

No current electrospinning methods exist that can create independent gradients in fiber alignment and chemistry along the length of the fibrous scaffold, in order words within the same layer of fiber deposition. Most electrospun fiber gradients are along the thickness of the scaffold by changing the processing parameters as the fibers are being deposited. Comparable manufacturing techniques that can create gradients in structure (like 3D printing), do not produce nanofibers as similar in structure to native tissue when compared to electrospinning techniques. More specifically, 3D printing is limited by the resolution of the printing needle and is typically larger than 1 um, whereas electrospinning produces fibers in the hundreds of nms. No current tissue engineering therapies exist that address interfacial tissue engineering. Current technology is mostly allograft/autograft tissue, which is limited by donor availability. The disclosed material/manufacturing process can create an unlimited amount of biocompatible, synthetic materials as scaffolds for tissue regeneration of interfacial tissue.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not. Further, it should further be noted that the terms "first," "second," and the like herein do not denote any order, quantity, or relative importance, but rather are used to distinguish one element from another.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated. All ranges disclosed herein are inclusive of the endpoints, and the endpoints are independently combinable with each other. Each range disclosed herein constitutes a disclosure of any point or sub-range lying within the disclosed range.

As used herein, the term "biomolecule" refers large macromolecules (or polyanions) such as proteins, carbohydrates, lipids, and nucleic acids, as well as small molecules such as primary metabolites, secondary metabolites, and nucleotides. The biomolecules may be isolated from a natural source or be synthetically produced. For example, a biomolecule may be a protein, a polypeptide, a peptide, a growth factor, a steroid, or a nucleic acid. Specific classes of biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

As used herein, the term "longitudinal composition gradient" refers to the plurality of fibers having a fiber composition gradient along the length of the fibrous material. For example, a plurality of fibers comprised within the same layer of the fibrous material can have a gradient fiber composition through the length of the layer.

As used herein, the term "longitudinal alignment gradient" refers to the plurality of fibers having a fiber alignment gradient along the length of the fibrous material. For example, a plurality of fibers comprised within the same layer of the fibrous material can have a gradient fiber alignment through the length of the layer.

As used herein, the term "metal nanoparticle" can refer to a nano-scale particle that is attracted or repelled by a magnetic field gradient or has a non-zero magnetic susceptibility. The metal nanoparticle can be of any shape, including but not limited to spherical, rod, elliptical, cylindrical, and disc.

As used herein, the term "musculoskeletal" refers to the bodily system that is made up of the bones of the skeleton, muscles, cartilage, tendons, ligaments, joints, and other connective tissue that supports and binds tissues and organs together.

As used herein, the terms "providing", "administering," and "introducing," are used interchangeably herein and refer to the placement of the compositions of the disclosure into a subject by a method or route which results in at least partial localization of the composition to a desired site. The compositions can be administered by any appropriate route which results in delivery to a desired location in the subject.

A "subject" or "patient" may be human or non-human and may include, for example, animal strains or species used as "model systems" for research purposes, such a mouse model as described herein. Likewise, patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

As used herein, "treat," "treating" and the like mean a slowing, stopping or reversing of progression of a disease or disorder when provided a composition described herein to an appropriate control subject. The terms also mean a reversing of the progression of such a disease or disorder to a point of eliminating or greatly reducing the cell proliferation. As such, "treating" means an application or administration of the compositions described herein to a subject, where the subject has a disease or a symptom of a disease, where the purpose is to cure, heal, alleviate, relieve, alter, remedy, ameliorate, improve or affect the disease or symptoms of the disease.

All documents cited herein and the following listed documents that are attached hereto for submission, all referenced publications cited therein, and the descriptions and information contained in these documents are expressly incorporated herein in their entirety to the same extent as if each document or cited publication was individually and expressly incorporated herein:

While the invention has been described with reference to preferred embodiments, it will be understood by those skilled in the art that various changes may be made and equivalents may be substituted for the elements thereof without departing from the scope of the invention. In addition, many modifications may be made to adapt the teaching of the invention to particular use, application, manufacturing conditions, use conditions, composition, medium, size, and/ or materials without departing from the essential scope and spirit of the invention.

While various aspects and embodiments have been disclosed herein, other aspects and embodiments will be apparent to those skilled in the art. The various aspects and embodiments disclosed herein are for purposes of illustration and are not intended to be limiting of the true scope of the invention disclosed herein. It is also to be understood that the terminology used herein is for the purpose of describing particular embodiments only, and is not intended to be limiting. Since many modifications, variations, and changes in detail can be made to the described examples, it is intended that all matters in the preceding description and shown in the accompanying figures be interpreted as illustrative and not in a limiting sense.

All methods described herein can be performed in any suitable order unless otherwise indicated herein or otherwise clearly contradicted by context. The use of any and all examples, or exemplary language (e.g., "such as"), is intended merely to better illustrate the invention and does not pose a limitation on the scope of the invention or any embodiments unless otherwise claimed.

2. FIBROUS MATERIALS

The present disclosure is directed to fibrous materials comprising a plurality of polymer fibers, wherein the plurality of fibers has a longitudinal alignment gradient of more than about 70% aligned to less than about 35% aligned. In some embodiments, the longitudinal alignment gradient may be more than about 70% aligned to less than about 35% aligned, more than about 75% aligned to less than about 30% aligned, more than about 80% aligned to less than about 20% aligned, more than about 85% aligned to less than about 15% aligned, more than about 90% aligned to less than about 10% aligned, or more than about 95% aligned to less than about 5% aligned. In some embodiments, the fibrous material may have a longitudinal composition gradient.

In some embodiments, the plurality of fibers may have an average diameter of less than 5 μm. For example, the plurality of fibers may have an average diameter of less than 4 μm, less than 3 μm, less than 2 μm, less than 1 μm, or less than 500 nm. In some embodiments, the plurality of fibers may have an average diameter between about 100 nm and about 5 μm, between about 500 nm and about 5 μm, between about 1 μm and about 5 μm, or between about 3 μm and about 5 μm. In some embodiments, the plurality of fibers may have an average diameter of about 100 nm, about 500 nm, about 1 μm, about 2 μm, about 3 μm or about 4 μm.

The fibers may be comprised of any polymer appropriate for electrospinning. In some embodiments, the plurality of polymer fibers are the same polymers. In some embodiments, the plurality of polymer fibers are different polymers. In some embodiments, the plurality of polymer fibers may each individually comprise a polymer selected from the group consisting of hyaluronic acid, polyethylene oxide, polyglycolic acid, polylactic acid, PLGA, polyolefin, polyacrylonitrile, polyurethane, polycarbonate, polycaprolactone, polyvinyl alcohol, cellulose, silk, polyaniline, polystyrene, chitosan, nylon, and combinations thereof.

In some embodiments, the polymer fiber may comprise a metal nanoparticle. Metal nanoparticles are a class of nanoparticle which can be manipulated using magnetic field and/or magnetic field gradient. Such nanoparticles commonly consist of magnetic elements such as iron, nickel and cobalt and their oxide compounds. Metal nanoparticles are well-known and methods for their preparation have been described in the art. See, e.g., U.S. Pat. Nos. 6,878,445; 5,543,158; 5,578,325; 6,676,729; 6,045,925; 7,462,446; 7,429,339; 7,459,145; 7,700,193; 8,557,607; and 10,564,228; and U.S. Patent Publications No. 2005/0025971; No. 2005/0201941; and No. 2007/0264199, the contents of which are incorporated herein by reference. Many different types of metal nanoparticles are also widely and commercially available.

In some embodiments, the magnetic particles can include any ferromagnetic material, paramagnetic material, superparamagnetic material or any combinations thereof. Ferromagnetic refers to materials having large and positive susceptibility to an external magnetic field. Ferromagnetic materials have some unpaired electrons so their atoms have a net magnetic moment. They exhibit a strong attraction to magnetic fields and are able to retain their magnetic properties for at least a period of time after the external field has been removed. Examples of ferromagnetic materials include, but are not limited to, iron, nickel and cobalt, Magnetite ($Fe_3O_4$), maghemite ($yFe_2O_3$), jacobsite ($MnFe_2O_4$), trevorite ($NiFe_2O_4$), magnesioferrite ($MgFe_2O_4$), pyrrhotite ($Fe_7S_8$), greigite ($Fe_3S_4$), feroxyhyte ($5FeOOH$), awaruite ($Ni_3Fe$), wairauite ($CoFe$), and any combinations thereof.

In some embodiments, the metal nanoparticles can include ferromagnetic particles, e.g., ferrous particles such as iron particles. In one embodiment, the iron particles can include carbonyl iron particles. Carbonyl iron is generally a highly pure iron (e.g., ~97.5% for grade S, ~99.5+% for grade R), prepared by chemical decomposition of purified iron pentacarbonyl. It is usually composed of spherical microparticles. Most of the impurities include, e.g., carbon, oxygen, and nitrogen. Carbonyl iron has also been used in pharmaceutical applications as iron supplements to treat iron deficiency. Even in non-anemic persons, high doses of carbonyl iron can be tolerated (Gordeuk, V et al., "Carbonyl iron therapy for iron deficiency anemia" Blood, 1986. 67 (3): 745-752). Thus, some embodiments of a fibrous material comprising carbonyl iron as magnetic particles can be used in vivo, e.g., for tissue engineering applications.

In some embodiments, the metal nanoparticles can include a paramagnetic material. Paramagnetic refers to materials having a small and positive susceptibility to magnetic fields, which are slightly attracted by a magnetic field. In some embodiments, paramagnetic materials do not retain magnetic properties when the external field is removed. These paramagnetic properties are due to the presence of some unpaired electrons and the realignment of the electron orbits caused by the external magnetic field. Examples of paramagnetic materials include, but are not limited to, magnesium, molybdenum, and lithium.

In some embodiments, the metal nanoparticles can include a superparamagnetic material. Superparamagnetic refers to the property of materials which have no permanent (equiaxed) alignment of the elementary magnetic dipoles in the absence of the action of external magnetic fields. In the presence of an external magnetic field, however, superparamagnetic materials can have magnetic susceptibilities at a level similar to ferromagnetic materials. Superparamagnetism can occur when the diameter of the crystalline regions in a normally ferromagnetic substance falls below a particular critical value. In some embodiments, the metal nanoparticles are superparamagnetic $Fe_3O_4$ nanoparticles.

In some embodiments, the metal nanoparticle may be of any size. In some embodiments, the metal nanoparticle may range in size from about 1 nm to about 100 nm. For example, magnetic particles can be about 1 nm to about 50 nm in size, or about 50 nm to about 100 nm in size, or about 25 nm to about 75 nm in size. In some embodiments, magnetic particles can be about 1 nm to about 90 nm, about 1 nm to about 70 nm, about 1 nm to about 50 nm, about 1 nm to about 30 nm, about 1 nm to about 10 nm, about 10 nm to about 80 nm, about 10 nm to about 60 nm, about 10 nm to about 40 nm, about 10 nm to about 20 nm, about 20 nm to about 60 nm, about 20 nm to about 40 nm, or about 40 nm to about 60 nm in size.

In some embodiments, the polymer fiber does not comprise a metal nanoparticle.

In some embodiments, the fibrous material may include a biomolecule, a drug molecule or a combination thereof. In some embodiments, the longitudinal composition gradient may include a biomolecule, a drug molecule or a combination thereof. In some embodiments, the polymer fiber comprises a biomolecule, a drug molecule or a combination thereof.

In some embodiments, the biomolecule may be a protein, peptide, polypeptide, steroid or nucleic acid. In some embodiments, the biomolecule may be a growth factor, cell adhesion sequence, an extracellular matrix component, cytokines, bioactive lipids, immunoglobulins, or any combination of these. For example, addition of fibronectin, integrins, or oligonucleotides that promote cell adhesion may be added to the fibrous materials. In some embodiments, chemotactic or anti-inflammatory agents may be added to the matrix to influence the behavior of cells in the tissue surrounding the fibrous material.

Particularly suitable biomolecules can be, for example, platelet derived growth factor (PDGF), transforming growth factor beta (TGFβ), vascular endothelial growth factor (VEGF), fibroblast growth factor (FGF), epidermal growth factor (EGF), human growth factor (HGF), bone morphogenetic proteins (BMPs), insulin-like growth factors (e.g., IGF-1 and IGF-2), keratinocyte growth factor, connective tissue growth factor, chemotactic proteins, sphingosine 1-phosphate (S1P), various macrophage and monocyte mediators such as RANTES (Regulated upon Activation, Normal T-cell Expressed, and Secreted), tumor necrosis factor α (TNF α), interferon gamma (IFNγ), and granulocyte-macrophage colony stimulating factor (GM-CSF), lipoxin and combinations thereof. Suitable cytokines can be, for example, interleukins (e.g., IL-1-IL-36) and interferons (e.g., interferon type I, interferon type II, interferon type III).

Drugs may include antibiotics, antivirals, chemotherapeutic agents, anti-angiogenic agents, hormones, drugs having an effect on vascular flow, anti-inflammatories, or many others known in the art.

a. Multicomponent Fibrous Materials

The present disclosure is also directed to fibrous materials comprising a plurality of polymer fibers comprising a first fiber and optionally a second fiber, wherein the fibrous material has a longitudinal composition gradient and the plurality of fibers has a longitudinal alignment gradient. In some embodiments, the fibrous materials include a first fiber but not a second fiber. In some embodiments, the fibrous material includes a first fiber and a second fiber.

In some embodiments, the plurality of fibers may have an average diameter of less than 5 μm. For example, the plurality of fibers may have an average diameter of less than 4 μm, less than 3 μm, less than 2 μm, less than 1 μm, or less than 500 nm. In some embodiments, the plurality of fibers may have an average diameter between about 100 nm and about 5 μm, between about 500 nm and about 5 μm, between about 1 μm and about 5 μm, or between about 3 μm and about 5 μm. In some embodiments, the plurality of fibers may have an average diameter of about 100 nm, about 500 nm, about 1 μm, about 2 μm, about 3 μm or about 4 μm.

In some embodiments, the first fiber may be present at about 0.1% to about 95% by weight in the fibrous material. In some embodiments, the first fiber may be present at about 1%, 10%, 20%, 30%, 40%, 50%, 60%, 70%, 80%, or 90% by weight in the fibrous material. In some embodiments, the second fiber may be present at about 0.1% to about 95% by weight in the fibrous material. In some embodiments, the second fiber may be present at about 1%, 10%, 20%, 30%, 40%, 50%, 60%, 70%, 80%, or 90% by weight in the fibrous material.

In some embodiments, the first fiber may be present at about 0.1% to about 95% by weight in the plurality of fibers. In some embodiments, the first fiber may be present at about 1%, 10%, 20%, 30%, 40%, 50%, 60%, 70%, 80%, or 90% by weight in the plurality of fibers. In some embodiments, the second fiber may be present at about 0.1% to about 95% by weight in the plurality of fibers. In some embodiments, the second fiber may be present at about 1%, 10%, 20%, 30%, 40%, 50%, 60%, 70%, 80%, or 90% by weight in the plurality of fibers.

The fibers may be comprised of any polymer appropriate for electrospinning. In some embodiments, the first fiber and the second fiber may be the same polymers. In some embodiments, the first fiber and the second fiber are different polymers. In some embodiments, the first and second fiber may each individually comprise a polymer selected from the group consisting of hyaluronic acid, polyethylene oxide, polyglycolic acid, polylactic acid, PLGA, polyolefin, polyacrylonitrile, polyurethane, polycarbonate, polycaprolactone, polyvinyl alcohol, cellulose, silk, polyaniline, polystyrene, chitosan, nylon, and combinations thereof.

The fibrous material may further comprise a third fiber. In some embodiments, the third fiber may be present at about 0.1% to about 95% by weight in the fibrous material. In some embodiments, the third fiber may be present at about 1%, 10%, 20%, 30%, 40%, 50%, 60%, 70%, 80%, or 90% by weight in the fibrous material. In some embodiments, the third fiber may be present at about 0.1% to about 95% by weight in the plurality of fibers. In some embodiments, the third fiber may be present at about 1%, 10%, 20%, 30%, 40%, 50%, 60%, 70%, 80%, or 90% by weight in the plurality of fibers.

In some embodiments, the third fiber may comprise a polymer selected from the group consisting of hyaluronic acid, polyethylene oxide, polyglycolic acid, polylactic acid, PLGA, polyolefin, polyacrylonitrile, polyurethane, polycarbonate, polycaprolactone, polyvinyl alcohol, cellulose, silk, polyaniline, polystyrene, chitosan, nylon, and combinations thereof. In some embodiments, the third fiber may be the same polymer as the first fiber or second fiber. In some embodiments, the third fiber may be a different polymer from the first fiber, the second fiber or both.

In some embodiments, at least one of the fibers may comprise a metal nanoparticle. Metal nanoparticles are a class of nanoparticle which can be manipulated using magnetic field and/or magnetic field gradient. Such nanoparticles commonly consist of magnetic elements such as iron, nickel and cobalt and their oxide compounds. Metal nanoparticles are well-known and methods for their preparation have been described in the art. See, e.g., U.S. Pat. Nos. 6,878,445; 5,543,158; 5,578,325; 6,676,729; 6,045,925; 7,462,446; 7,429,339; 7,459,145; 7,700,193; 8,557,607; and 10,564,228; and U.S. Patent Publications No. 2005/0025971; No. 2005/0201941; and No. 2007/0264199, the contents of which are incorporated herein by reference. Many different types of metal nanoparticles are also widely and commercially available.

In some embodiments, the magnetic particles can include any ferromagnetic material, paramagnetic material, superparamagnetic material or any combinations thereof. Ferromagnetic refers to materials having large and positive susceptibility to an external magnetic field. Ferromagnetic materials have some unpaired electrons so their atoms have a net magnetic moment. They exhibit a strong attraction to magnetic fields and are able to retain their magnetic properties for at least a period of time after the external field has been removed. Examples of ferromagnetic materials include, but are not limited to, iron, nickel and cobalt, Magnetite ($Fe_3O_4$), maghemite ($\gamma Fe_2O_3$), jacobsite ($MnFe_2O_4$), trevorite ($NiFe_2O_4$), magnesioferrite ($MgFe_2O_4$), pyrrhotite ($Fe_7Ss$), greigite ($Fe_3S_4$), feroxyhyte ($5FeOOH$), awaruite ($Ni_3Fe$), wairauite ($CoFe$), and any combinations thereof.

In some embodiments, the metal nanoparticles can include ferromagnetic particles, e.g., ferrous particles such as iron particles. In one embodiment, the iron particles can include carbonyl iron particles. Carbonyl iron is generally a highly pure iron (e.g., ~97.5% for grade S, ~99.5+% for grade R), prepared by chemical decomposition of purified iron pentacarbonyl. It is usually composed of spherical microparticles. Most of the impurities include, e.g., carbon, oxygen, and nitrogen. Carbonyl iron has also been used in pharmaceutical applications as iron supplements to treat iron deficiency. Even in non-anemic persons, high doses of carbonyl iron can be tolerated (Gordeuk, V et al., "Carbonyl iron therapy for iron deficiency anemia" Blood, 1986. 67 (3): 745-752). Thus, some embodiments of a fibrous material comprising carbonyl iron as magnetic particles can be used in vivo, e.g., for tissue engineering applications.

In some embodiments, the metal nanoparticles can include a paramagnetic material. Paramagnetic refers to materials having a small and positive susceptibility to magnetic fields, which are slightly attracted by a magnetic field. In some embodiments, paramagnetic materials do not retain magnetic properties when the external field is removed. These paramagnetic properties are due to the presence of some unpaired electrons and the realignment of the electron orbits caused by the external magnetic field. Examples of paramagnetic materials include, but are not limited to, magnesium, molybdenum, and lithium.

In some embodiments, the metal nanoparticles can include a superparamagnetic material. Superparamagnetic refers to the property of materials which have no permanent (equiaxed) alignment of the elementary magnetic dipoles in the absence of the action of external magnetic fields. In the presence of an external magnetic field, however, superparamagnetic materials can have magnetic susceptibilities at a level similar to ferromagnetic materials. Superparamagnetism can occur when the diameter of the crystalline regions in a normally ferromagnetic substance falls below a particular critical value. In some embodiments, the metal nanoparticles are superparamagnetic $Fe_3O_4$ nanoparticles.

In some embodiments, the metal nanoparticle may be of any size. In some embodiments, the metal nanoparticle may range in size from about 1 nm to about 100 nm. For example, magnetic particles can be about 1 nm to about 50 nm in size, or about 50 nm to about 100 nm in size, or about 25 nm to about 75 nm in size. In some embodiments, magnetic particles can be about 1 nm to about 90 nm, about 1 nm to about 70 nm, about 1 nm to about 50 nm, about 1 nm to about 30 nm, about 1 nm to about 10 nm, about 10 nm to about 80 nm, about 10 nm to about 60 nm, about 10 nm to about 40 nm, about 10 nm to about 20 nm, about 20 nm to about 60 nm, about 20 nm to about 40 nm, or about 40 nm to about 60 nm in size.

In some embodiments, the first fiber, the second fiber, or a combination thereof, may include a metal nanoparticle. In some embodiments, at least one of the fibers does not include a metal nanoparticle. In some embodiments, none of the fibers includes a metal nanoparticle.

In some embodiments, the fibrous material may include a biomolecule, a drug molecule or a combination thereof. In some embodiments, the longitudinal composition gradient may include a biomolecule, a drug molecule or a combination thereof. In some embodiments, at least one of the fibers individually comprises a biomolecule, a drug molecule or a combination thereof.

In some embodiments, the biomolecule may be a protein, peptide, polypeptide, steroid or nucleic acid. In some embodiments, the biomolecule may be a growth factor, cell adhesion sequence, an extracellular matrix component, cytokines, bioactive lipids, immunoglobulins, or any combination of these. For example, addition of fibronectin, integrins, or oligonucleotides that promote cell adhesion may be added to the fibrous materials. In some embodiments, chemotactic or anti-inflammatory agents may be added to the matrix to influence the behavior of cells in the tissue surrounding the fibrous material.

Particularly suitable biomolecules can be, for example, platelet derived growth factor (PDGF), transforming growth factor beta (TGFβ), vascular endothelial growth factor (VEGF), fibroblast growth factor (FGF), epidermal growth factor (EGF), human growth factor (HGF), bone morphogenetic proteins (BMPs), insulin-like growth factors (e.g., IGF-1 and IGF-2), keratinocyte growth factor, connective tissue growth factor, chemotactic proteins, sphingosine 1-phosphate (S1P), various macrophage and monocyte mediators such as RANTES (Regulated upon Activation, Normal T-cell Expressed, and Secreted), tumor necrosis factor α (TNF α), interferon gamma (IFNγ), and granulocyte-macrophage colony stimulating factor (GM-CSF), lipoxin and combinations thereof. Suitable cytokines can be, for example, interleukins (e.g., IL-1-IL-36) and interferons (e.g., interferon type I, interferon type II, interferon type III).

Drugs may include antibiotics, antivirals, chemotherapeutic agents, anti-angiogenic agents, hormones, drugs having an effect on vascular flow, anti-inflammatories, or many others known in the art.

In some embodiments, at least one of the fibers individually comprises a biomolecule, a drug molecule or a combination thereof. In some embodiments, the first fiber, the second fiber, the third fiber, or a combination thereof, comprises a biomolecule, a drug molecule or a combination thereof. In some embodiments, the biomolecule or drug may be linked to the fibers through a covalent bond or a non-covalent bond, e.g., a hydrogen bond, an electrostatic interaction, a hydrophobic interaction, or a van der Waals interaction.

In one embodiment, the disclosure provides a fibrous material comprising a plurality of fibers, the plurality of fibers including a first fiber; and a second fiber comprising a metal nanoparticle, wherein the plurality of fibers have a longitudinal composition gradient and a longitudinal alignment gradient.

In another embodiment, the disclosure provides a method of preparing a fibrous material comprising a plurality of fibers, the method comprising electrospinning a first fiber and a second fiber comprising a metal nanoparticle onto a collector having a first portion and a second portion to provide a fibrous material as disclosed herein, wherein at least one portion of the collector comprises at least one magnet.

3. METHODS OF PREPARING FIBROUS MATERIALS

The present disclosure is directed to methods of preparing the disclosed fibrous materials described above. Described herein is a method of magnetically-assisted, optionally combined with multicomponent, electrospinning in order to create bioinspired, magnetically-responsive gradient materials (MRGMs). Through the innovative combination of electrospinning methods, independent spatial control over fiber alignment using an applied magnetic field and chemistry using offsetting polymer jets is possible. Furthermore, multicomponent, magnetically-assisted electrospinning creates fibrous scaffolds with gradients in magnetic nanoparticle concentration allowing for spatially controlled, stimuli-responsive behavior in the presence of an external magnetic field. See FIG. 6 for a schematic of the novel magnetically-assisted multicomponent electrospinning technique according to one embodiment of the disclosure.

a. Magnetic Electrospinning

Figure 8:
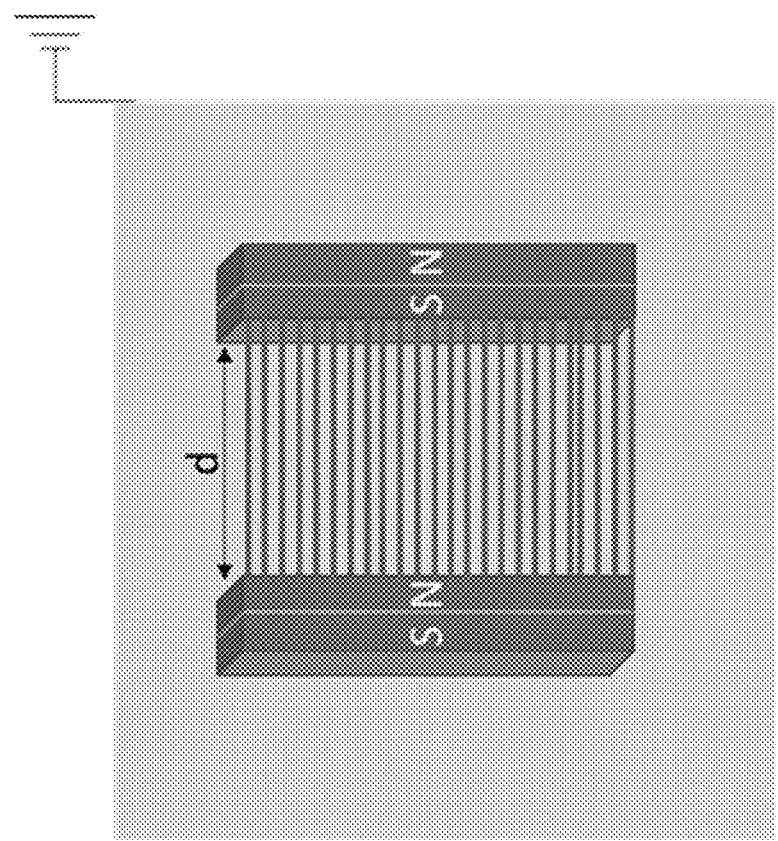
FIG. 8 shows magnetic electrospinning diagrams displaying magnetic field strength and direction when attractive magnets are horizontally separated and electrospun fibers (green) aligning in the direction of the magnetic field between two magnets with distance, d.
Figure 8:
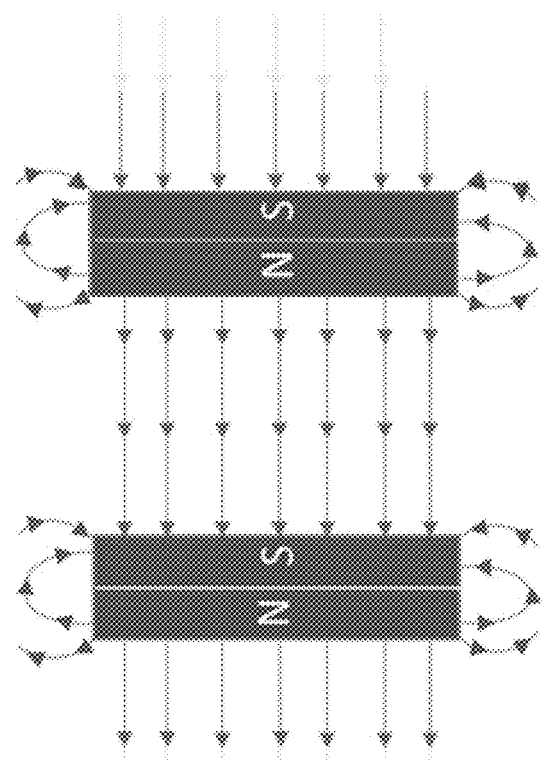

Magnetic electrospinning is one technique for producing highly aligned fibrous materials. Magnetic electrospinning can be used to induce fiber alignment in the direction of a magnetic field produced from permanent magnets. This strategy utilizes the magnetic field strength of two permanent bar magnets, where fibers will align in the direction of the magnetic field between the magnets (FIG. 8).

Figure 4A:
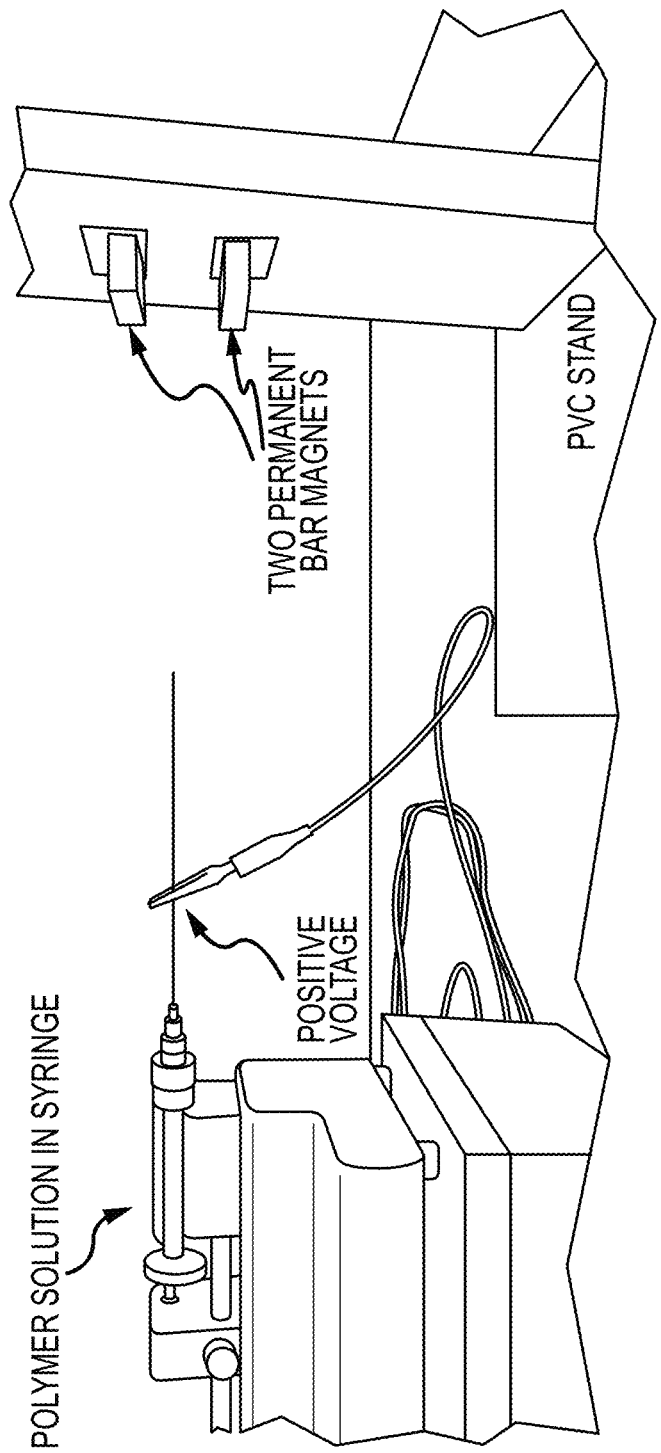
FIGS. 4A-4B show magnetically-assisted electrospinning. Magnetically-assisted electrospinning setup uses two bar magnets and a flat collection plate (FIG. 4A). Schematic representation of electrospun fiber alignment gradient resulting from applied magnetic field. Black arrows indicate direction and strength of the magnetic field and N and S corresponding to the magnetic poles (FIG. 4B).
Figure 4B:
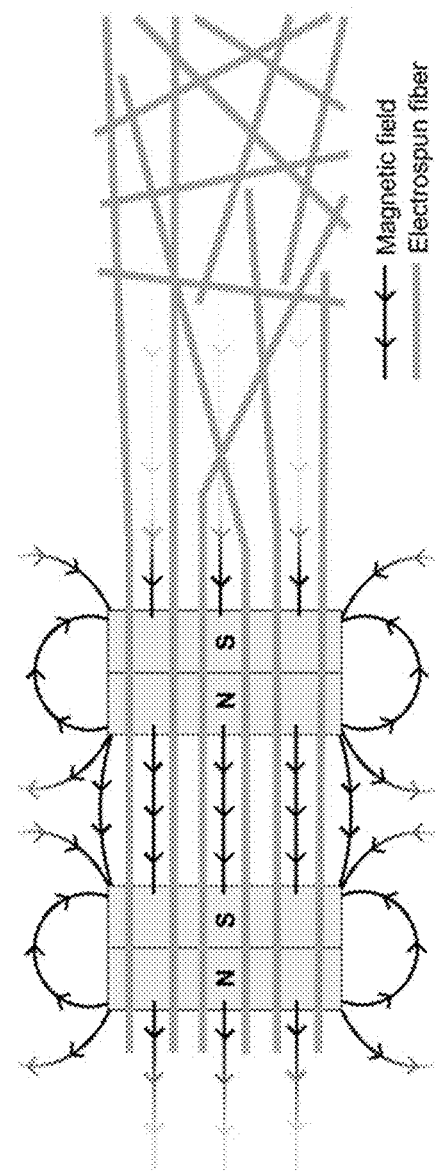

In magnetically-assisted electrospinning, a magnetic field is generated during electrospinning using parallel-positioned permanent magnets as shown in FIGS. 4A and 4B. At sufficient magnetic field strengths and nanoparticle concentrations, electrospun fibers will align in the direction of the magnetic field. Depending on electrospinning polymer type, magnetic nanoparticles may need to be added to the electrospinning solution to result in fiber alignment and responsiveness to the magnetic field. Additionally, electrospun fibrous scaffolds containing magnetic nanoparticles continue to be responsive to external magnetic fields after electrospinning. These magnetically-responsive materials react by moving in the direction of an external magnetic field, with the degree of movement dependent on magnetic field strength. Materials that are responsive to external magnetic fields allow for spatiotemporal control over the delivery of localized mechanical forces with potential implications in spatially controlling cellular behavior for heterogeneous tissue engineering.

The present disclosure is directed to a method of preparing a fibrous material comprising a plurality of polymer fibers. The method includes electrospinning a polymer fiber onto a collector (such as a mandrel) having a first portion and a second portion to provide a fibrous material, wherein at least one portion of the collector comprises a magnetic field. The fibrous material comprises a plurality of polymer fibers, wherein the plurality of fibers has a longitudinal alignment gradient of more than about 70% aligned to less than about 35% aligned, as described above. In some embodiments, the longitudinal alignment gradient may be more than about 70% aligned to less than about 35% aligned, more than about 75% aligned to less than about 30% aligned, more than about 80% aligned to less than about 20% aligned, more than about 85% aligned to less than about 15% aligned, more than about 90% aligned to less than about 10% aligned, or more than about 95% aligned to less than about 5% aligned. In some embodiments, the fibrous material may have a longitudinal composition gradient.

In some embodiments, at least one of the fibers can include a metal nanoparticle. In some embodiments, the magnetic field may be created by at least one magnet. In some embodiments, the magnetic field is created by one, two, three, four or five magnets. In certain embodiments, the magnetic field is created by one magnet. In certain embodiments, the magnetic field is created by two magnets. In some embodiments, the magnets are applied along the portion of the rotating collector or mandrel with poles alternating along the width. In some embodiments, the magnets can be wrapped around the circumference of the rotating collector or mandrel and positioned parallel to one another. In some embodiments, the magnets are applied to generate a magnetic field force oriented along the axis of the rotating collector or mandrel.

In some embodiments, the applied magnetic field may be greater than or equal to about 1 mT. In some embodiments, the applied magnetic field may be greater than or equal to about 10 mT, about 20 mT, about 50 mT, about 100 mT, about 150 mT, about 200 mT, or about 250 mT. The applied magnetic field may be about 1 mT, about 25 mT, about 50 mT, about 75 mT, about 100 mT, about 150 mT, about 200 mT, or about 250 mT. In some embodiments, the applied magnetic field may be between 1 mT and 250 mT, between 5 mT and 200 mT, between 10 mT and 200 mT, or between 10 mT and 150 mT.

In some embodiments, the electrospinning can be performed using the following approximate parameters: +24 kV applied voltage, 1.2 mL/hr polymer flow rate, and 16 cm spinneret to collector or mandrel distance. In some embodiments, the applied voltage can be about +10 kV, about +15 kV, about +20 kV, about +21 kV, about +22 kV, about +23 kV, about +24 kV, about +25 kV, about +26 kV, about +27 kV, about +30 kV, about +35 kV, about +40 kV, or about +50 kV. In some embodiments, the polymer flow rate can be about 0.5 mL/hr, about 1.0 ml/hr, about 1.1 mL/hr, about 1.2 ml/hr, about 1.3 mL/hr, about 1.4 ml/hr, about 1.5 mL/hr, about 2.0 ml/hr, about 2.5 mL/hr, about 3.0 ml/hr, about 4.0 mL/hr, or about 5.0 ml/hr. In some embodiments, the spinneret to collector or mandrel distance can be about 5 cm, about 10 cm, about 11 cm, about 12 cm, about 13 cm, about 14 cm, about 15 cm, about 16 cm, about 17 cm, about 18 cm, about 19 cm, or about 20 cm. In some embodiments, barriers can be used on either side of the collector or mandrel to control where each fiber component collects onto the collector or mandrel. In some embodiments, the collector or mandrel can have a rotation speed between 0.1 m/g to about 5 m/s, such as about 1 m/s. In some embodiments, the collector can be a flat plate. In some embodiments, the collector can be a flat plate that is not rotating.

b. Multicomponent Electrospinning

In multicomponent electrospinning, several independent polymer jets, with a distinct polymer solution in each jet, are electrospun onto a common rotating mandrel in order to fabricate scaffolds with multiple, discrete, polymer fiber fractions. The resulting multicomponent fibrous scaffold is a composite material with each individual fiber fraction maintaining its independent properties and the overall scaffold reflecting the combination of those fiber fractions. Multicomponent electrospinning can be used to fabricate tri-component fibrous scaffolds (PCL: poly(ε-caprolactone), PEO: poly(ethylene oxide), and HA: hyaluronic acid) for biphasic biomolecule delivery towards improving endogenous meniscus cell migration and repair.

c. Combining Multicomponent and Magnetic Electrospinning

The present disclosure is directed to methods of preparing the disclosed fibrous materials comprising a plurality of fibers using the combination of multicomponent and magnetic electrospinning. The method includes electrospinning a first fiber and optionally a second fiber onto a collector (such as a mandrel) having a first portion and a second portion to provide a fibrous material described herein, wherein at least one portion of the collector comprises a magnetic field. The manufacturing of structurally and chemically gradient fibrous materials uses a novel magnetically-assisted, multicomponent electrospinning technique. In some embodiments, the method includes electrospinning a first fiber but not a second fiber. In some embodiments, the method includes electrospinning a first fiber and a second fiber.

In some embodiments, at least one of the fibers can include a metal nanoparticle. In some embodiments, the first fiber, the second fiber, or a combination thereof, can include a metal nanoparticle. The metal nanoparticle may be as described above.

In some embodiments, the magnetic field may be created by at least one magnet. In some embodiments, the magnetic field is created by one, two, three, four or five magnets. In certain embodiments, the magnetic field is created by one magnet. In certain embodiments, the magnetic field is created by two or more magnets. In some embodiments, the magnets are applied along the portion of the rotating collector or mandrel with poles alternating along the width. In some embodiments, the magnets can be wrapped around the circumference of the rotating collector or mandrel and positioned parallel to one another. In some embodiments, the magnets are applied to generate a magnetic field force oriented along the axis of the rotating collector or mandrel. In some embodiments, the magnets are applied onto or along a flat plate collector.

In some embodiments, the applied magnetic field may be greater than or equal to about 1 mT. In some embodiments, the applied magnetic field may be greater than or equal to about 10 mT, about 20 mT, about 50 mT, about 100 mT, about 150 mT, about 200 mT, or about 250 mT. The applied magnetic field may be about 1 mT, about 25 mT, about 50 mT, about 75 mT, about 100 mT, about 150 mT, about 200 mT, or about 250 mT. In some embodiments, the applied magnetic field may be between 1 mT and 250 mT, between 5 mT and 200 mT, between 10 mT and 200 mT, or between 10 mT and 150 mT.

In some embodiments, electrospinning the first fiber and the second fiber may be done simultaneously or sequentially. In some embodiments, the first fiber is electrospun onto the first portion of the collector and the second fiber is electrospun onto the second portion of the collector. In certain embodiments, the method further includes electrospinning a third fiber onto the collector. In some embodiments, the third fiber may be electrospun simultaneously or sequentially with the first and/or second fibers.

In some embodiments, the electrospinning can be performed using the following approximate parameters: +24 kV applied voltage, 1.2 mL/hr polymer flow rate, and 16 cm spinneret to collector or mandrel distance. In some embodiments, the applied voltage can be about +10 kV, about +15 kV, about +20 kV, about +21 kV, about +22 kV, about +23 kV, about +24 kV, about +25 kV, about +26 kV, about +27 kV, about +30 kV, about +35 kV, about +40 kV, or about +50 kV. In some embodiments, the polymer flow rate can be about 0.5 mL/hr, about 1.0 ml/hr, about 1.1 mL/hr, about 1.2 ml/hr, about 1.3 mL/hr, about 1.4 ml/hr, about 1.5 mL/hr, about 2.0 ml/hr, about 2.5 mL/hr, about 3.0 ml/hr, about 4.0 mL/hr, or about 5.0 ml/hr. In some embodiments, the spinneret to collector or mandrel distance can be about 5 cm, about 10 cm, about 11 cm, about 12 cm, about 13 cm, about 14 cm, about 15 cm, about 16 cm, about 17 cm, about 18 cm, about 19 cm, or about 20 cm. In some embodiments, barriers can be used on either side of the collector or mandrel to control where each fiber component collects onto the collector or mandrel. In some embodiments, the collector or mandrel can have a rotation speed between 0.1 m/g to about 5 m/s, such as about 1 m/s. In some embodiments, the collector can be a flat plate. In some embodiments, the collector can be a flat plate that is not rotating.

d. Conjugation of Biomolecule to Fibrous Material

The disclosed fibrous material may further include a biomolecule. In some embodiments, the method of preparing the fibrous material may further include photoconjugating a biomolecule to the fibrous material. In some embodiments, the biomolecule is photoconjugated to the fibrous material after electrospinning.

In some embodiments, the biomolecule may be photoconjugated to the polymer fiber by photo treating the fibrous material or by photo treating the polymer fiber. In some embodiments, the biomolecule is photoconjugated to the fibrous material using UV light or visible light. In some embodiments, the biomolecule may be photoconjugated to at least one polymer fiber. In some embodiments, the biomolecule is photoconjugated to the first fiber and/or the second fiber using UV light or visible light. In some embodiments, the method further includes using at least one photo-opaque mask to create at least one longitudinal gradient in the biomolecule conjugation.

In some embodiments, the biomolecule is photoconjugated to the fiber by photo treating the fibrous material or by photo treating the first fiber, the second fiber, optionally the third fiber, or a combination thereof. In some embodiments, the biomolecule may be photoconjugated to at least one of the fibers using UV light or visible light. In some embodiments, the biomolecule is photoconjugated to the first fiber, the second fiber, the third fiber, or a combination thereof, using UV light or visible light. In some embodiments, the method further includes using at least one photo-opaque mask to create at least one longitudinal gradient in the biomolecule conjugation.

In some embodiments, photoconjugation may be carried out at any wavelength necessary to form the intermolecular covalent bond between the biomolecule and the polymer. In some embodiments, photoconjugation may use visible light from 400-700 nm, ultraviolet (UV) light from 10 nm-400 nm or a combination thereof. In some embodiments, the biomolecule is photoconjugated to the fiber by UV treating the fibrous material or by UV treating the first fiber, the second fiber, the third fiber, or a combination thereof.

4. METHODS OF USE

The present disclosure is directed to a method of treating organ or tissue damage in a subject. The method includes introducing a fibrous material as described herein into a subject in need thereof at or near the organ or tissue. In some embodiments, the organ or tissue may be any in which it is suitable to use the new viable in vitro alternative to a tissue or organ graft, for example, bone, cartilage, blood vessels, bladder, skin, muscle, and others. In some embodiments, any ligament or any tendon to bone tissue interface is targeted with the disclosed fibrous material.

In some embodiments, the organ or tissue is musculoskeletal tissue. Musculoskeletal injuries and diseases are a significant health concern in the United States, with recent reports citing as many as 1.6 million bone grafts implanted per year, 1 million meniscal surgeries performed per year, and a total of 27 million people currently living with osteoarthritis. Current treatments typically rely on donor tissues or removal of the damaged tissue. Regardless of the treatment option, most injured tissues never regain complete functionality, which can cause mild to severe degeneration of the surrounding tissues. In some embodiments, the tissue or organ is the rotator cuff. In some embodiments, the fibrous material is applied as a patch and sutured onto the injured rotator cuff.

5. EXAMPLES

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present disclosure has multiple aspects, illustrated by the following non-limiting examples.

Example 1: Multicomponent Electrospinning

Multicomponent electrospinning was used to create gradients in fiber chemistry by offsetting the polymer jets along the axis of the collector. In FIG. 3, fluorescently labeled fibers show the presence of three distinct fiber fractions, where degradation of each fiber fraction and corresponding biomolecule release was time-dependent and occurred independently of each other. Collagenase was released in a burst fashion to allow local degradation of the dense ECM and increased cell mobility, followed by moderate release of platelet-derived growth factor-AB (PDGF-AB) to direct endogenous cell migration to the injury. This showcased the ability of multicomponent electrospinning to fabricate fibrous scaffolds with independently tailorable fiber fractions.

Example 2: MRGMs with Independently Controlled Gradients in Fiber Alignment and Chemistry Multicomponent electrospinning was combined with magnetically-assisted electrospinning to create fibrous scaffolds with independent control over gradients in fiber alignment and chemistry. Magnetically-assisted electrospinning of a single fiber component was performed to showcase the ability of a controlled magnetic field to create gradients in fiber alignment along the length of the fibrous scaffold (FIG. 4A). As shown in FIGS. 5B-FIG. 5D, electrospun fibers were aligned (81% aligned) in the direction of the magnetic field close to the magnets and gradually transitioned to randomly aligned (28% aligned) away from the magnetic field. Magnetically-assisted electrospinning allowed for a gradient in fiber alignment along the length of the fibrous scaffold similar to the natural heterogeneity present in ligament or tendon to bone interfaces (FIG. 1).

Figure 6A:
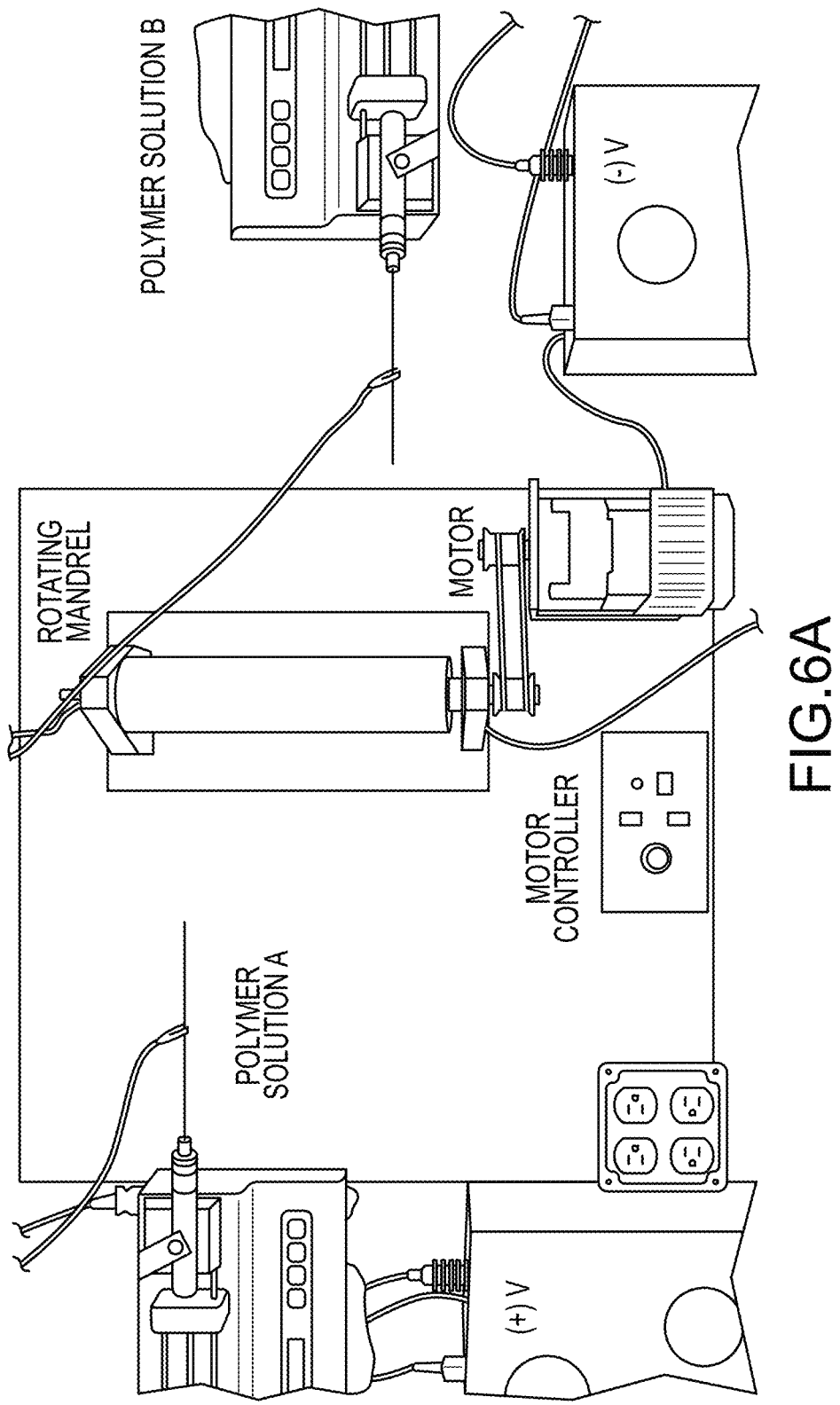

Multicomponent electrospinning is combined with magnetically-assisted electrospinning as depicted in FIGS. 6A-6C. For electrospinning, hyaluronic acid (HA), a naturally occurring polysaccharide, is selected due to its combination of bioactivity and synthetic versatility. To create gradients in fiber chemistry, the osteogenic growth peptide (OGP), which has been shown to promote osteogenesis, is selectively coupled to HA. The electrospun fibrous scaffold groups that is fabricated and characterized are detailed in Table 1 with uniform scaffolds without gradients as controls. Bioinspired MRGM platform for understanding and controlling cell-material interactions and mechanical loading in a heterogeneous environment is developed. Synthesis of fibrous scaffolds with gradients in fiber alignment via magnetically-assisted electrospinning using a single fiber component is demonstrated.

HEMA-HA Synthesis. Sodium hyaluronate (74 kDa; Lifecore Biomedical) is functionalized with hydroxyethyl methacrylate (HEMA) to allow for hydrolysis (via ester groups) and photo-initiated cross-linking (via methacrylate groups). The carboxylic acid modified HEMA is coupled to the tetrabutylammonium (TBA) salt of HA in anhydrous dimethyl sulfoxide for 20 hours at 45° C. using 4-dimethylaminopyridine (DMAP) and di-tert-butyl dicarbonate ($BOC_2O$) as coupling agents. HEMA-HA is purified via extensive dialysis, lyophilized, and analyzed with 1H NMR to determine HEMA functionalization percent (% f). 30% f HEMA-HA is synthesized using the following molar ratios: HA-TBA (1), HEMA-COOH (3), $BOC_2O$ (0.59), and DMAP (0.75). The cell adhesive peptide, RGD (GCGYGRGDSPG (SEQ ID NO: 1), italics indicate the cell adhesive domain; Genscript), is conjugated to HEMA-HA via an addition reaction between the thiol within the cysteine residue on the peptide and the methacrylate on HEMA-HA. For conjugation, 1 mM RGD is added to 2 wt % HEMA-HA dissolved in triethanolamine buffer for 4 hours at 4° C., dialyzed for 48 hours, and lyophilized.

Fabricating MRGMs Using Innovative Multicomponent, Magnetically-Assisted Electrospinning Technique. Fibrous scaffolds with independent gradients in fiber alignment and chemistry is synthesized using a multicomponent, magnetically-assisted electrospinning technique. All of the electrospinning solutions are made using the same HA solution ("base"): 4 wt % HEMA-HA and 2 wt % poly(ethylene oxide) (PEO) in 0.05 wt % Irgacure 2959 (photoinitiator), where PEO helps contribute to electrospinning stability. Next, either superparamagnetic Fe3O4 nanoparticles or OGP (GCALKRQGRTLYGFGG (SEQ ID NO: 2), italics indicate bioactive osteogenic domain; Genscript) are added to create the aligned or osteogenic scaffold components, respectively. OGP is conjugated to HEMA-HA at a concentration between 1 (low) to 5 (high) mM using the same protocol as previously described for RGD conjugation. To create gradients in fiber alignment and chemistry, two, offset, polymer solutions is simultaneously electrospun onto opposite ends of a rotating cylindrical mandrel as shown in FIG. 6.

Mandrel rotation speed is minimal (~1 m/s) to maintain mixing of the two fiber components. Electrospinning is performed using the following approximate parameters: +24 kV applied voltage, 1.2 mL/hr polymer flow rate, and 16 cm spinneret to mandrel distance. Plastic, non-conductive, barriers will be used on either side of the mandrel to control where each fiber component collects onto the mandrel and the resulting degree of overlap (or "interface region") between the two fiber components.

To induce fiber alignment, a local magnetic field is selectively applied along a portion of the rotating mandrel using two or more flexible, permanent magnetic adhesive strips with poles alternating along the width or face of the adhesive (custom manufactured, Adams Magnetic Products). The magnetic strips are wrapped around the circumference of the rotating mandrel and positioned parallel to each other (FIG. 6B). Utilizing this setup, the magnetic field force is oriented along the axis of the rotating mandrel and induces fiber alignment along the length of the fibrous scaffold. The force of the magnetic field is controlled using magnet size (thickness and width) and distance between the magnets, using a gauss meter and magnetic viewing paper to measure and visualize the magnetic field, respectively. The size of the aligned fiber component is controlled by adding additional magnetic strips in "series" along the length of the rotating mandrel.

Preliminary research using large bar magnets indicated fiber alignment occur in the presence of a magnetic field strength as low as 50 mT. Using this field strength as a starting point, magnetically-assisted electrospinning onto a rotating collector will be completed using several combinations of magnet configurations (number of magnet strips: 2-5, magnet thickness: 0.03-0.125 in., magnet width: 0.01-0.5 in.) and nanoparticle concentrations in HA solution (0.1-5 wt % Fe3O4). After electrospinning, fibrous scaffolds will be exposed to 10 mW/cm2 of ultraviolet light under nitrogen for 15 minutes on each side in order to crosslink the methacrylate groups within the HA fibers. Uniform scaffolds of each fiber component will serve as material controls, see Table 1 for a complete listing of all fibrous scaffold groups that will be synthesized and characterized in this objective and future objectives.

Electrospun Fibrous Scaffold Characterization. To verify gradients in overall scaffold fiber alignment, scanning electron microscopy (SEM; available at LeRoy Eyring Center for Solid State Science (LECSSS)) is performed and dry fiber diameter and alignment is calculated as a function of scaffold position. The fiber diameter and alignment of the individual fiber components is visualized and evaluated by doping the electrospinning polymer solutions with fluorescent dyes and imaging using fluorescent microscopy (similar to FIG. 3B). ImageJ software is used to measure fiber diameter and quantify fiber alignment of each fiber fraction as a function of scaffold position. Beyond visualization of the gradient in fiber alignment, fluorescent doping will also allow visual confirmation of gradients in fiber chemistry. To further quantify the gradient in fiber chemistry, X-ray photoelectron spectroscopy (XPS; available at LECSSS) may be performed as a function of scaffold position. XPS spectra will be collected in the 100-1000 eV bonding energy range, with a 1.0 eV resolution and a pass energy of 100 eV. Surface atomic chemical compositions and ratios will be determined via peak area analysis as a function of scaffold position.

Statistical Analysis. For all experiments, analysis of variance (ANOVA) was performed using SYSTAT, with Tukey's HSD post-hoc testing of differences between electrospun fibrous scaffold groups and as a function of scaffold position with α=0.05.

TABLE 1

Electrospun Fibrous Scaffold Groups

| Fibrous Scaffold Group | Polymer Solution A | Polymer Solution B |
|---|---|---|
| Gradient in alignment | Base (HA) | Aligned (HA + $Fe_3O_4$) |
| Gradient in chemistry | Osteogenic (HA + OGP) | Base (HA) |
| Gradient in alignment and chemistry | Osteogenic (HA + OGP) | Aligned (HA + $Fe_3O_4$) |
| Uniform controls | Base (HA); Aligned (HA + $Fe_3O_4$); Osteogenic (HA + OGP) | |

This shows the development and optimization of an innovative, multicomponent, magnetically-assisted electrospinning technique that allows for independent control of gradients in fiber alignment and chemistry along the scaffold length. The experiments provide an understanding of the relationship between electrospinning conditions (e.g. magnet size and configuration, nanoparticle concentration, OGP concentration, etc.) and gradient formation. The resulting bioinspired MRGMs can serve as a platform for evaluating cell-material interactions and mechanical loading in a heterogeneous environment in the remaining objectives.

Example 3: Spatially Control Stem Cell Spreading and Differentiation on MRGMs

MRGMs served as a platform for understanding and controlling mesenchymal stem cell (MSC) behavior in a bioinspired, heterogeneous environment. MSCs are of particular interest due to their capacity for differentiation, including most musculoskeletal cell types, and immunomodulation. The different electrospun fibrous scaffold groups from Table 1 were fabricated with varying concentrations of OGP (1, 3, and 5 mM) to determine the influence of fiber gradients in alignment and chemistry on MSC behavior. MSC behavior was characterized using cell viability, proliferation, spreading, and gene expression assays detailed in the methods below. Furthermore, cellular behavior was quantified as a function of location along scaffold length, with each scaffold segmented into three areas: segment A (primarily polymer A), AB (interfacial region) and B (primarily polymer B).

Figure 15A:
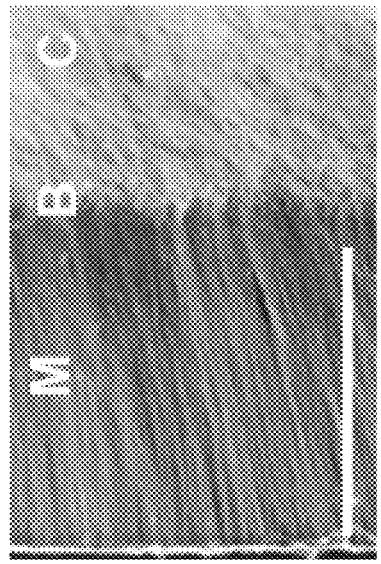
FIGS. 15A-15D show that filament alignment increases with magnetic field strength. A schematic of magnetic electrospinning onto a rotating collection mandrel (FIG. 15A). A macroscopic image showing transition from aligned to unaligned region (FIG. 15B, scale=1 cm).
Figure 15B:
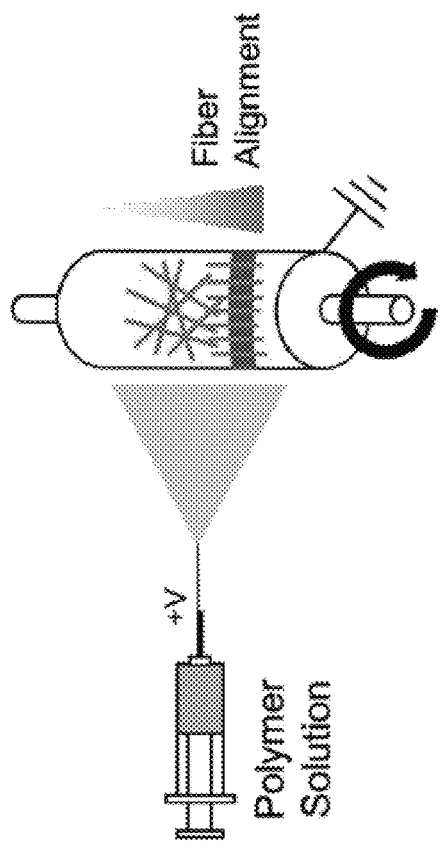
Figure 15C:
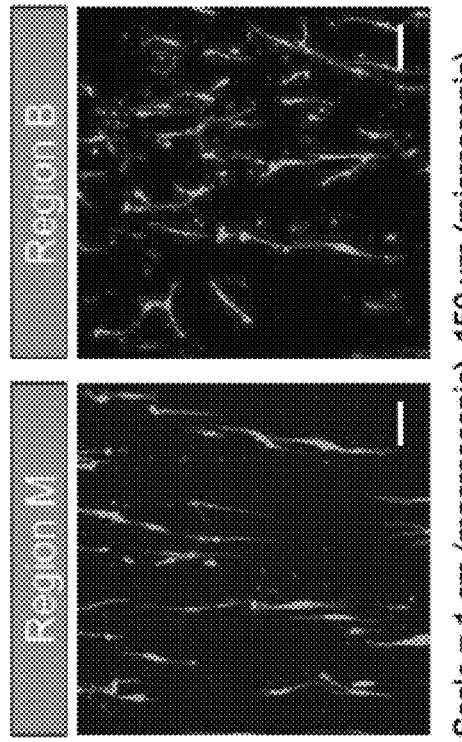
Figure 15D:
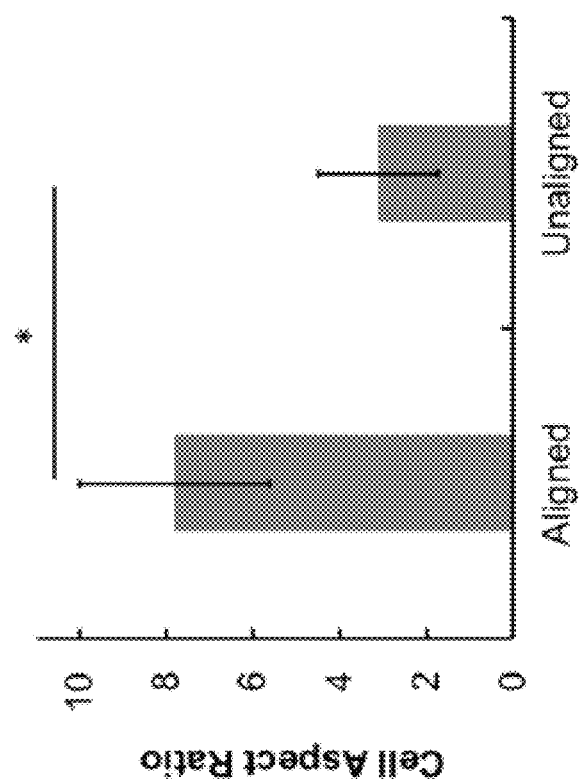

As shown in FIG. 15C and FIG. 15D, stem cells that are seeded onto the fibrous scaffolds align on the aligned portion of the scaffolds with a higher cell area aspect ratio and are more circular with a lower cell area aspect ratio on the unaligned portion of the scaffolds.

Cell Culture. Human MSCs (hMSCs, Lonza) were cultured and passaged using standard cell culture protocols. For seeding onto fibrous scaffolds, a cell suspension of hMSCs was seeded onto fibrous scaffolds at an approximate concentration of 20,000 cells per $cm^2$ in growth media by direct addition of the cell suspension onto the fibrous scaffold. After seeding, scaffolds were incubated at 37° C. and 5% $CO_2$ for up to three weeks to allow time for cells to adhere, spread, and differentiate in response to gradients in fiber alignment and/or chemistry. After 1, 3, 7, 14, and 21 days of culture, cell viability (live/dead assay) and proliferation (BrdU assay) on the fibrous scaffolds will be determined.

Cell Size, Shape, and Focal Adhesions. To image and quantify cell size, shape, and focal adhesions, samples after 1, 3, 7, 14, and 21 days of culture (as described above) were fixed and stained for actin cytoskeleton (phalloidin), nuclei (DAPI), and vinculin (primary monoclonal mouse anti-human vinculin and secondary FITC-conjugated goat anti-mouse) using standard techniques. NIH's ImageJ software will be used to quantify cell spreading from the actin cytoskeleton stain. The vinculin stain was used as a measure of the number and organizational level of the focal adhesions.

Gene Expression. Quantitative real-time polymerase chain reaction (RT-PCR) is performed after 7, 14, and 21 days of cell culture using standard techniques to quantify gene expression. Relative gene expression is calculated using the $\Delta\Delta CT$ method with GAPDH as a housekeeping gene. The following genes are used as markers for bone (alkaline phosphatase, bone sialoprotein, osteocalcin, and osteopontin), tendon/ligament (collagen type I, decorin, biglycan, and tenascin C), and cartilage (type II collagen, aggrecan, and sox-9).

The new knowledge gained from these experiments may be critical for developing innovative biomaterials-based approaches to regenerating complex, multicellular tissues, particularly interfacial tissues with similar gradients in fiber alignment and chemistry. Specifically, gradients in fiber chemistry and alignment can enable spatial control of hMSC spreading and differentiation, with higher cell aspect ratios and increased ligament and/or tendon gene expression on the aligned areas of the fibrous scaffolds and lower cell aspect ratios and increased osteogenic gene expression on the osteogenic (OGP functionalized) area of the fibrous scaffolds. In the event of limited osteogenesis, higher OGP functionalization or other osteogenic biomolecules can be investigated, including bone morphogenetic protein-2 peptides.

Example 4: Local, Heterogeneous, Biomechanical Behavior of MRGMs

The local, heterogeneous biomechanical behavior of MRGMs was studied and compared to the uniform control scaffolds to determine the local strain behavior of gradient materials during bulk tensile testing using digital image correlation and spatiotemporally deliver mechanical forces to cell-seeded MRGMs. The local biomechanical behavior of these materials is critical, as complex tissues typically have heterogeneous mechanical behavior that is important for tissue function. In particular, interfacial tissues are responsible for transferring mechanical load from one tissue type to another, where the presence of high stress concentration at this interface can result in failure.

Figures 16A, 16B:
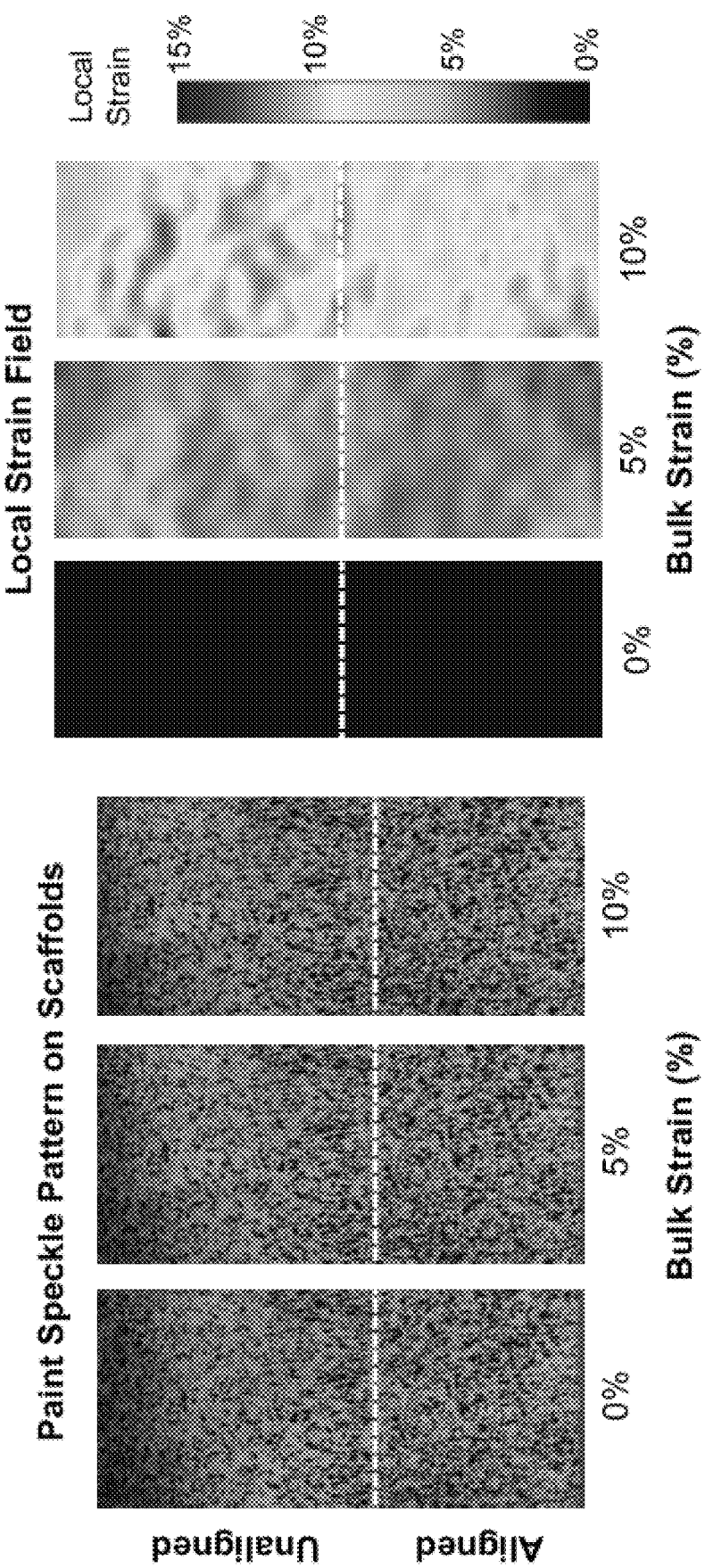
FIGS. 16A-16B show local strain analysis during tensile testing of gradient electrospun fibrous scaffolds.

Bulk Tensile Testing with Local Strain Analysis. Digital image correlation was used to measure the local strain profile of electrospun fibrous scaffolds during tensile testing. Briefly, dry fibrous scaffolds (30×5×0.5 mm) was marked with an array of dots (15×5) using an acid free ink pen to create an array of black markers on a white surface (see FIG. 16A). High speed video, with a frame rate of 10 per s, was used to capture the motion of the markers during tensile testing, as well as the failure mechanism. For tensile testing, samples were placed in serrated grips, preloaded at 0.5 N, and extended to failure at 0.1% strain/second using an Instron 5942 Microtester and a 50 N load cell. The following mechanical properties was calculated for each test: tensile modulus (slope of the linear region of the stress-strain curve), ultimate tensile strength (peak stress before failure), toughness (area under the stress-strain curve before failure), and strain at failure.

Figure 17B:
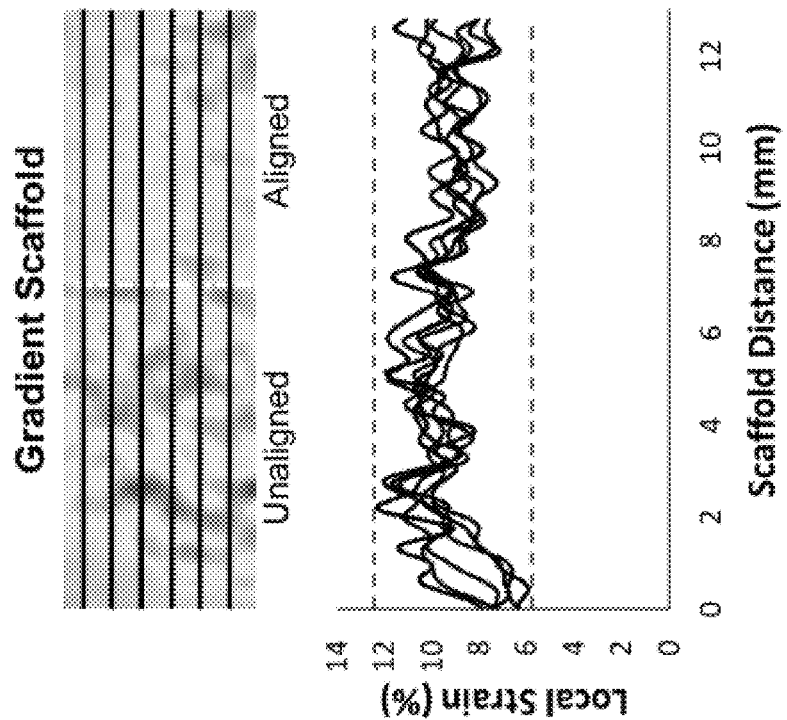
FIGS. 17A-17B show local strain analysis during tensile testing of gradient electrospun fibrous scaffolds.
Figure 17A:
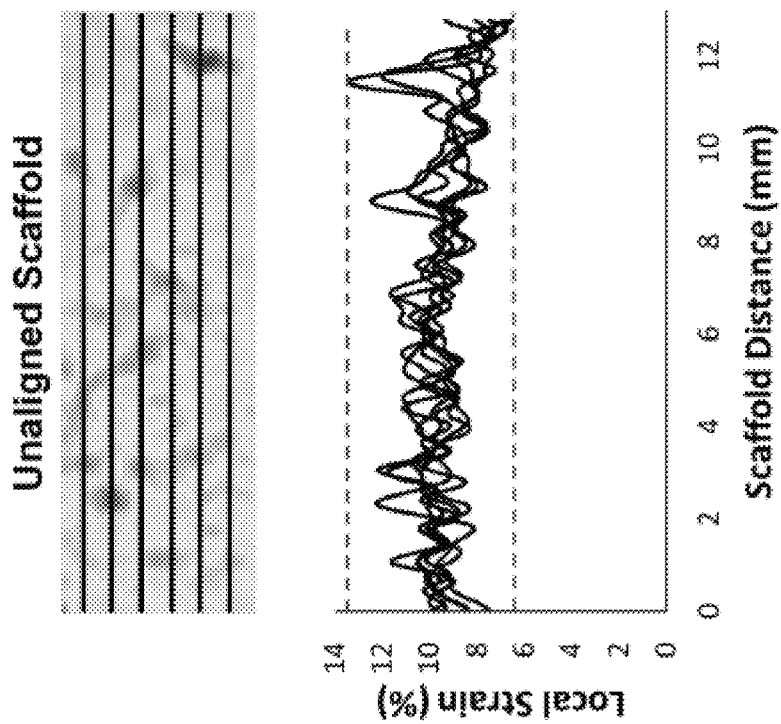
Figure 18E:
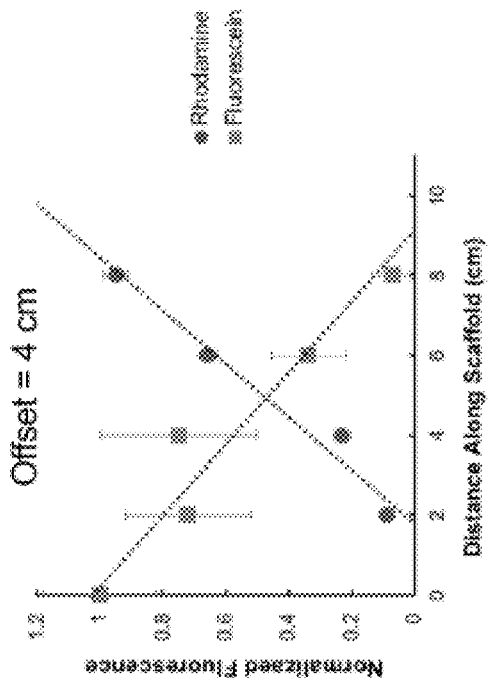
Figure 18D:
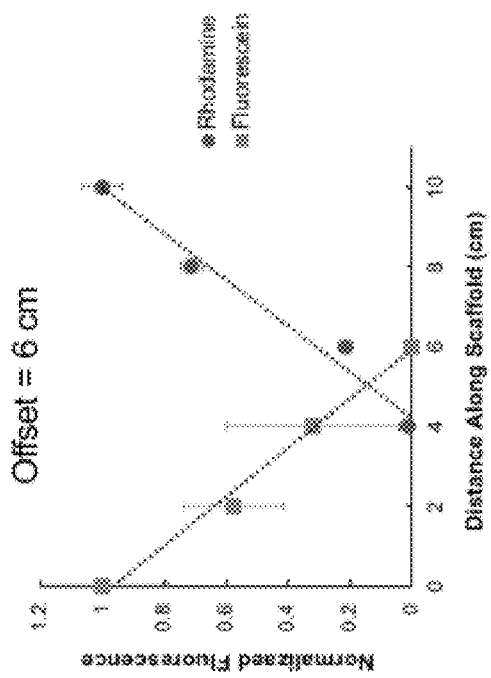

Strain contour plots were then generated using multiphysics modeling software, LS-DYNA (Livermore Software Technology Corporation). From the contour plots, the maximum local strain was identified, as well as the slope of the maximum strain gradient across the sample length. In FIG. 16, typical images of the gradient fibrous scaffold with markers for tracking strain and the local strain analysis is shown for up to 10% bulk tensile strain. Analysis of the local strain along the scaffold length shows gradient scaffolds do not exhibit higher local strains at the interface between the aligned and unaligned region (FIG. 17).

Spatiotemporally Deliver Mechanical Forces to Cell-Seeded MRGMs. External magnetic fields will be generated using permanent bar magnets and used to deliver localized, spatially controlled mechanical forces to the MRGMs. Electrospun fibrous scaffolds will be taped onto glass slides to keep the fibers spread out and placed in four-well cell culture plates. Human MSCs will be seeded onto the fibrous scaffolds with intermittent external magnetic field stimulation by arranging two permanent bar magnets on either side of the cell culture plate. Magnetic field stimulation will occur once a day for times between ten min and four hours, for three weeks. Cellular behavior as a function of fibrous scaffold group and scaffold location will be assessed, including: cell viability and proliferation; cell size, shape, and focal adhesions; and gene expression.

Fibrous scaffolds with gradients in fiber chemistry and without nanoparticles are not expected to show any spatially-dependent biomechanical behavior or respond to magnetic stimuli. MRGMs with gradients in fiber alignment are expected to have a heterogeneous strain behavior along the length of the scaffold. Furthermore, the presence of magnetic nanoparticles within these materials should allow spatiotemporal delivery of local mechanical forces via external magnetic field stimulation. Mechanical stimulation of hMSCs is expected to have a significant effect on cell behavior, particularly proliferation and differentiation. Depending on the observed cellular response, the magnetic field strength can be increased or decreased by varying magnet volume and the time and frequency of the intermittent external magnetic field stimulation can be altered. It is expected there will be an optimal magnetic field strength and stimulation frequency allowing for spatiotemporal control of hMSC behavior while maintaining high cell viability.

Example 5: Electrospun Fibers with Fiber Alignment Gradients Using Magnetic Electrospinning Every standard permanent magnet creates a local magnetic field with decreasing magnetic field strength at increasing distances from the magnet. Electrospun fibers generated a fiber alignment gradient, with highly aligned fibers at moderate magnetic field strengths (~25 mT) and decreasing fiber alignment as the magnetic field strength weakens at distances away from the magnet (FIG. 9A). Fibrous samples were electrospun onto aluminum foil for 5 minutes and sectioned into regions A, B, and C at increasing distances away from the magnet as indicated in FIG. 9B. Scanning electron microscopy (SEM) images and quantification of fiber alignment confirmed the fibrous scaffold contained a fiber alignment gradient with region A, B, and C having 81±6%, 52±7%, and 27±9% fiber alignment, respectively (FIGS. 9C and 9D).

Example 6: Fiber Alignment Gradient with Different Magnet Configurations

Figure 10:
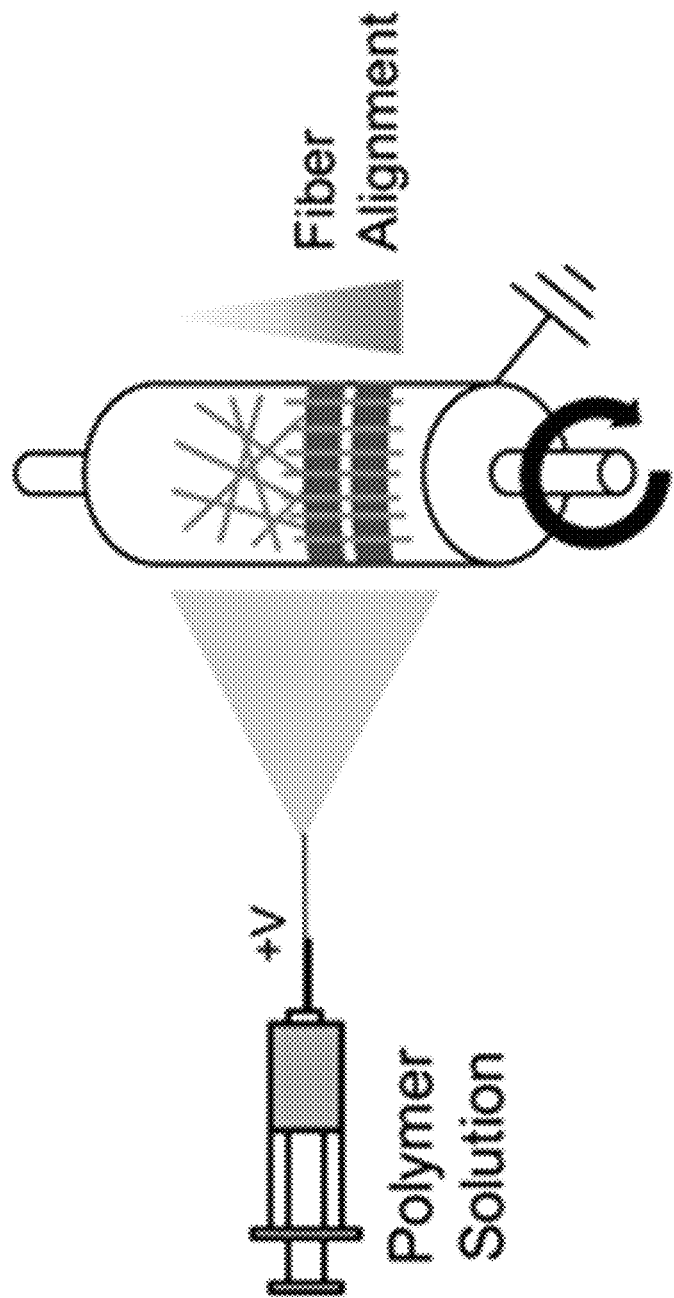
FIG. 10 shows magnetic electrospinning onto a rotating collection mandrel. Schematic of two magnet strips adhered onto a rotating collection mandrel during electrospinning.

Tuning Length of Highly Aligned Fiber Region. It is desired to have both a fiber alignment gradient as well as a chemistry gradient. To accomplish this task, fibers were spun onto a rotating collection mandrel to allow for mixing of two independent polymer electrospinning components. These two components were offset from each other along the length of the collection mandrel, creating a chemistry gradient independently of a fiber alignment gradient. Through an innovative combination of magnetic electrospinning and offset electrospinning, the fiber alignment section was controlled with magnetic field strength and direction, and the chemistry gradient was controlled by the degree of offset between the two polymer electrospinning solutions. To modify the previous work for a rotating collector, magnet strips provided by Adams Magnets (6"×0.5"×0.03") were magnetized through the width of the material (FIG. 10A) and adhered onto a grounded rotating collection mandrel (FIG. 10B). Magnetic field strength on the surface of the strip was measured to be approximately 26 mT.

Figure 11A:
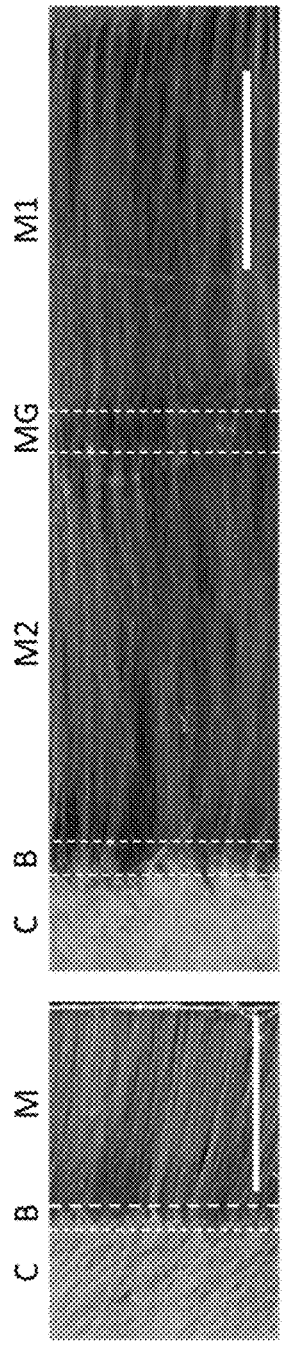
FIGS. 11A-11E show fiber alignment as a function of magnet configuration. Macroscopic images (FIG. 11A) of fibrous samples using one magnet strip (left) or two magnets in series (right), scale=1 cm. Bright field images and fiber quantification of one magnet (FIG. 11B and FIG. 11D) or two magnets in series (FIG. 11C, FIG. 11E), scale=150 μm. The fiber alignment of each region was statistically significant from all other regions unless otherwise noted with N.S. Regions are labeled as follows: M (magnet), M1 (magnet 1), M2 (magnet 2), MG (gap between magnets), B (transition region), or C (away from magnets).
Figure 11B:
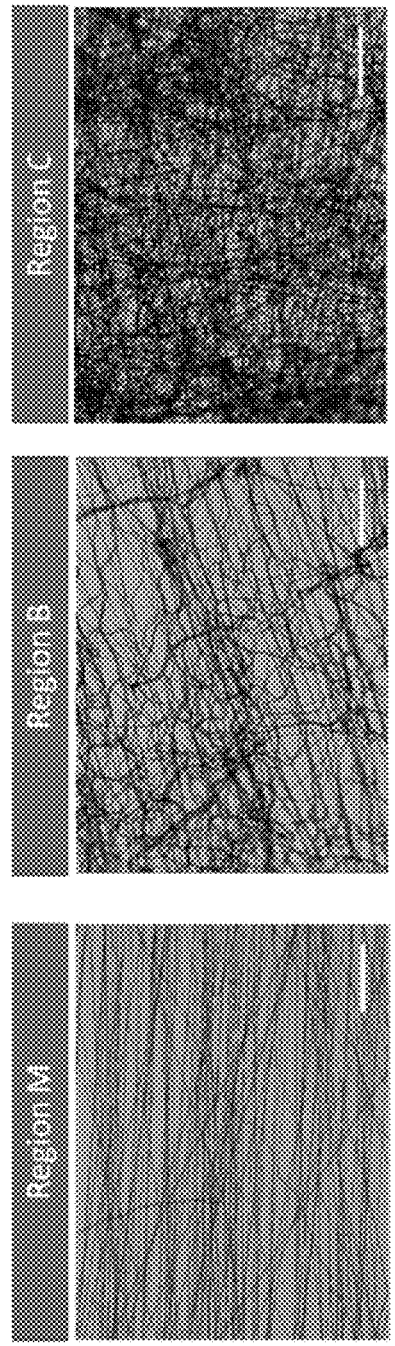
Figure 11C:
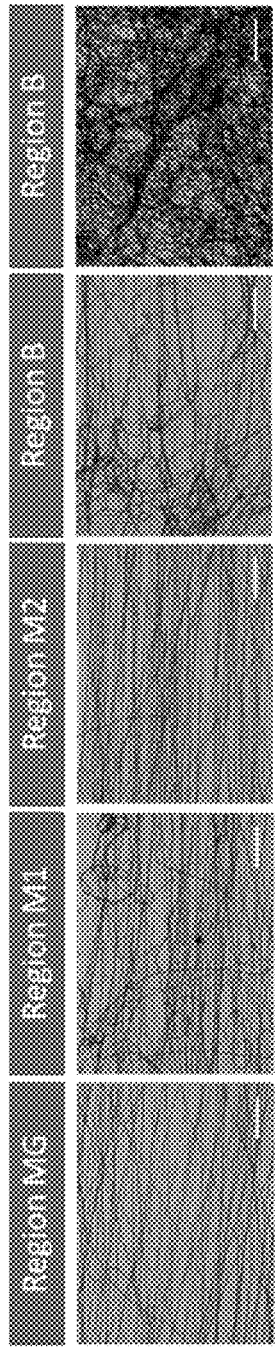
Figure 11E:
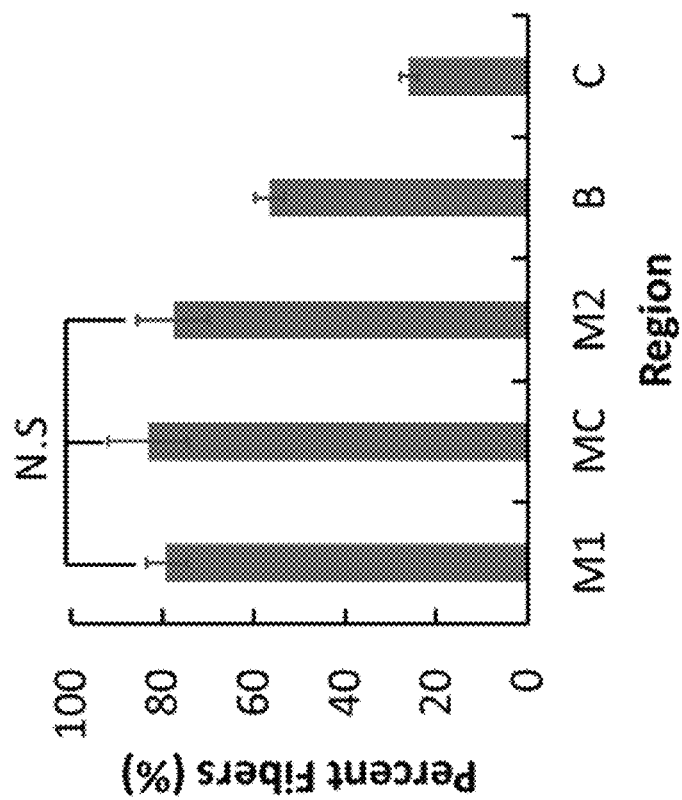
Figure 11D:
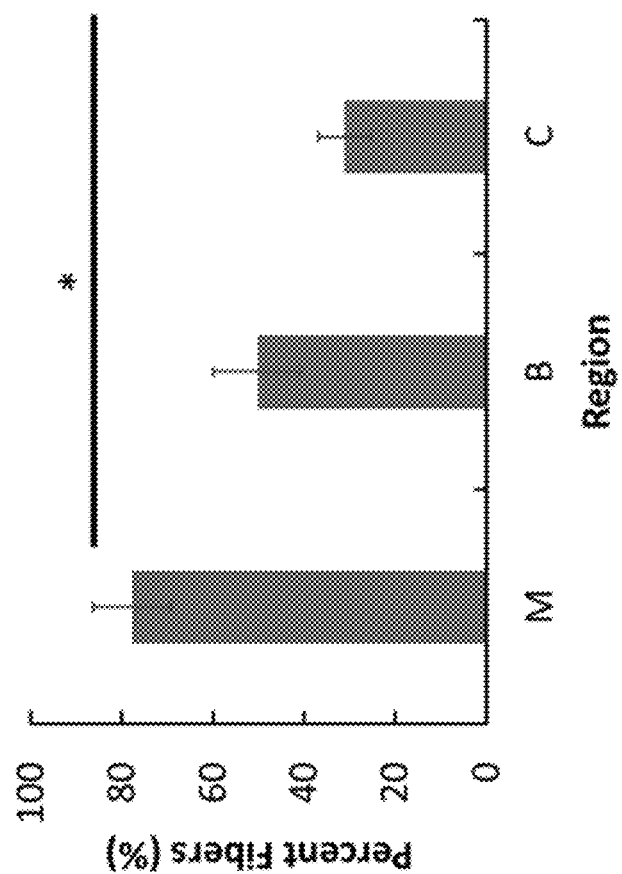

Altering the number of magnets next to each other or in "series" can generate various lengths of the highly aligned fiber region of the scaffold. One magnet induced a length of 0.5 inches of highly aligned fibers (FIG. 11A, left), whereas two magnets in series generated 1 inch of highly aligned fibers (FIG. 11A, right). To quantify the fiber alignment for a single magnet, fibrous samples were electrospun for 5 minutes and were sectioned into regions M (magnet), B (transition region), and C (away from the magnet) (FIG. 11A, B). Similarly, for two magnets in series, samples were sectioned into M1 (magnet 1), MG (3 mm gap between magnets), M2 (magnet 2), B (transition region), and C (away from magnets) (FIG. 11A, C). Bright field microscopy was used to quantify fiber alignment for one magnet or two magnets in series (FIG. 11B, C). In both cases a similar trend was observed, with the highly aligned fiber regions indicating over 70% fiber alignment, the transition regions between 50-60% fiber alignment, and the unaligned region away from the magnet less than 35% fiber alignment (FIG. 11B, C). As a result, the exact width of the magnet and the number of magnets in series were changed to tailor the length of the highly aligned fiber region.

Creating Complex Fiber Alignment Gradients. A novel aspect of this electrospinning technique is the ability to spatially control the location and size of the highly aligned and unaligned fiber regions through precise control of the local magnetic field strength. For example, by placing magnets far apart, alternating regions of highly aligned fibers (aligned/unaligned/aligned) were generated (FIG. 12).

Figure 12:
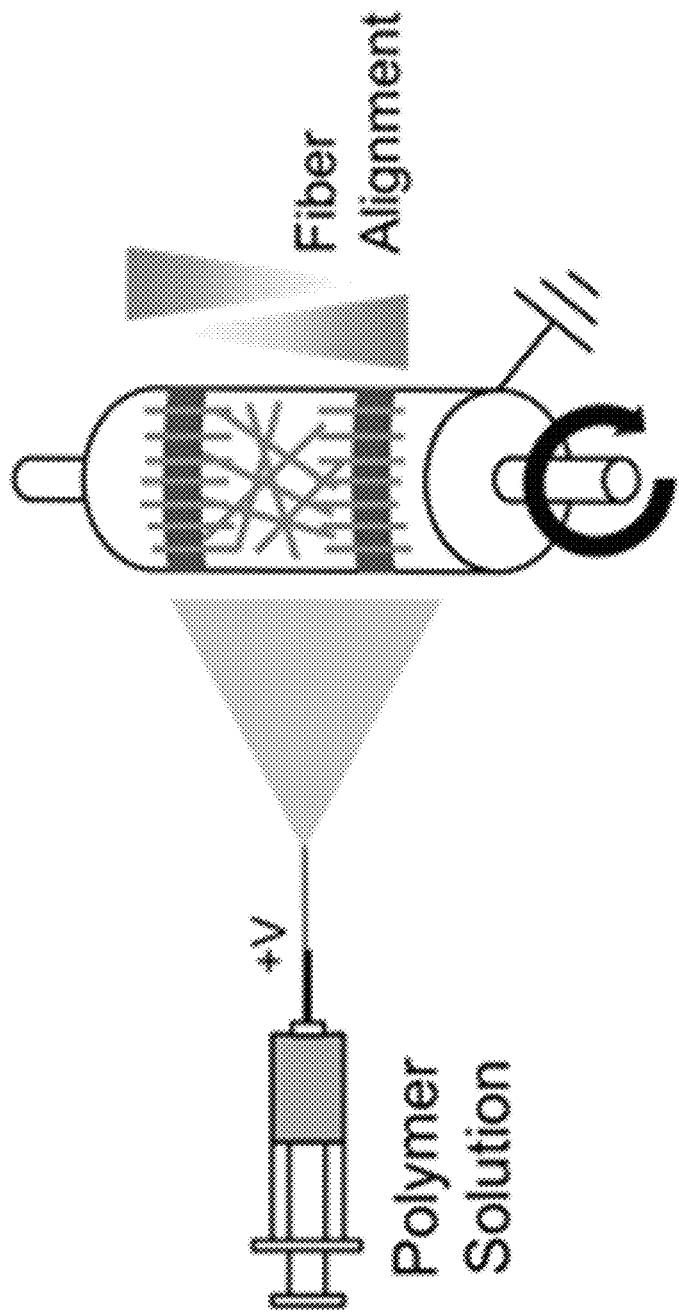
FIG. 12 shows a schematic of manipulating various types of alternating fiber alignments. Two magnets separated far enough will formulate an aligned-unaligned-unaligned fibrous orientation.

Applying the scheme shown in FIG. 12, this concept was tested with two magnets separated one cm apart. Samples were electrospun for 5 minutes and sectioned into regions M1 (magnet 1), B1 (transition region 1), C (center of two magnets), B2 (transition region 2) and M2 (magnet 2) (FIG. 13A). Bright field microscopy and fiber alignment quantification confirmed fibers transitioned from highly aligned, to unaligned, to highly aligned from one magnet to the other (FIGS. 13B and 13C). Thus, this innovative magnetic electrospinning design enabled the fabrication of complex fiber alignment structures.

Fabricating a fiber alignment gradient through magnetic electrospinning was achieved. A standard permanent magnet produced a magnetic field gradient enabling electrospun fibers to form a fiber alignment gradient with increasing alignment at higher magnetic field strengths. Therefore, fibers were highly aligned on the surface and close to the magnet, and began to unalign with increasing distances away from the magnet. Furthermore, this novel magnetic electrospinning technique allowed for tailoring of the length of the highly aligned region, as well as for more complex fiber alignment gradients (i.e. aligned-unaligned-aligned).

Example 7: Structurally Graded Fibrous Scaffolds for Improved Interfacial Tissue Regeneration A majority of musculoskeletal tissue engineering research has focused on the regeneration of one particular tissue type (i.e. bone, cartilage, ligament) and neglected to address the musculoskeletal tissue interfaces that serve as the connection between these tissues. Musculoskeletal tissue interfaces, such as the cartilage-bone and ligament-bone interface, gradually transition from one orthopedic tissue to another and often possess distinct physical and biological properties compared to the connecting tissues. Furthermore, musculoskeletal tissue interfaces play an important biomechanical role efficiently transferring load between orthopedic tissues. Typical surgical repair methods to treat musculoskeletal tissue injuries fail to adequately regenerate the necessary interfacial tissue, resulting in inferior biomechanical function and ultimately compromising long-term clinical outcome. Structurally graded fibrous scaffolds can be developed in order to better understand cellular behavior in the presence of physical gradients and to lend insight into biomaterial design for improved interfacial tissue regeneration.

Figure 14:
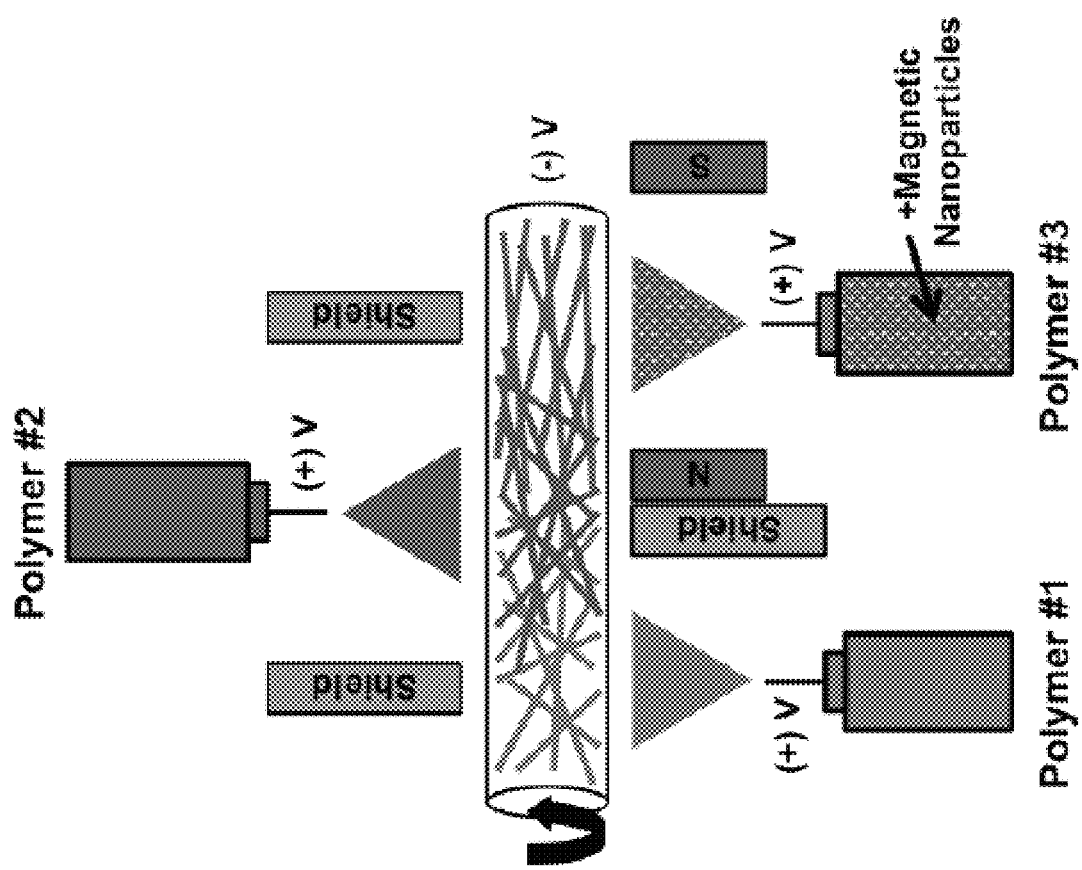
FIG. 14 shows a schematic detailing multicomponent magnetic electrospinning set-up.

Compared to traditional hydrogels, electrospun scaffolds better model the fibrous nature of the native ECM, where variation of the electrospinning parameters allows for easy tailoring of the scaffold morphology. Graded fibrous scaffolds can be synthesized through tri-component electrospinning using the set-up depicted in FIG. 14. Polymer spinnerets will be aligned along the length of the cylindrical collection mandrel, with the presence of positively charged shields to control the boundary of each individual material component. For magnetic electrospinning, a small amount (<0.5 wt %) of magnetic nanoparticles will be added to the polymer solution, using highly biocompatible superparamagnetic iron oxide nanoparticles. The magnetic field will be generated using two parallel-positioned, permanent magnets, with fiber alignment occurring in the direction of the magnetic field. Scaffold fiber morphology can be evaluated using scanning electron microscopy and fluorescent microscopy techniques, where individual fiber fractions will be visualized by doping the polymer solutions with separate fluorophores.

Multi-component magnetic electrospinning can be used to synthesize fibrous hyaluronic acid (HA) scaffolds with gradients in (1) mechanics, (2) alignment, and (3) both mechanics and alignment along the length of the scaffold material. Gradients in scaffold mechanical properties will be created through variation of the cross-linking density of each fibrous component and gradients in alignment via a combination of mandrel rotation speed and the application of a magnetic field. Cellular behavior will be evaluated using both co-culture (osteoblasts and fibroblasts) and single culture (mesenchymal stem cell) conditions. Cell phenotype, shape, alignment, density, and gene expression will be used to compare cellular behavior along scaffold gradients and as a function of culture time. Video strain analysis can be used to assess scaffold mechanical integrity before and after in vitro cell culture. This evaluation is critical, as the localization of high stresses or strains along gradient materials can cause failure.

Example 8: Bioinspired, Gradient Fibrous Materials with Independent Spatial Control Over Fiber Alignment and Chemistry, and Capable of Mimicking Native Tendon to Bone Interfacial Tissue An innovative magnetically-assisted electrospinning technique may be combined with biomolecular photoconjugation to create fibrous scaffolds with independent control over gradients in fiber alignment and chemistry. For electrospinning, hyaluronic acid (HA), a naturally occurring polysaccharide, was selected due to its combination of bioactivity and synthetic versatility. To create gradients in fiber chemistry, the osteogenic growth peptide (OGP), which has been shown to promote osteogenesis, can be selectively coupled to HA through photoconjugation after electrospinning. To mimic the tendon to bone interfacial tissue, an aligned fiber region or the "tendon mimetic region" will gradually transition to an unaligned fiber region with OGP or the "bone mimetic region". The electrospun fibrous scaffold groups that will be fabricated and tested are detailed in Table 1 with uniform, homogeneous scaffolds without gradients as controls. An important part of the scaffold characterization will be determination of the local strain behavior of the gradient materials during bulk tensile testing. The local biomechanical behavior of these materials is critical, as the organization of the scaffold or regenerated tissue may impact the stress vs strain behavior during loading. Interfacial tissues are responsible for transferring mechanical load from one tissue type to another, where the presence of high stress concentration at tendon to bone interface has been linked to failure.

Figure 2B:
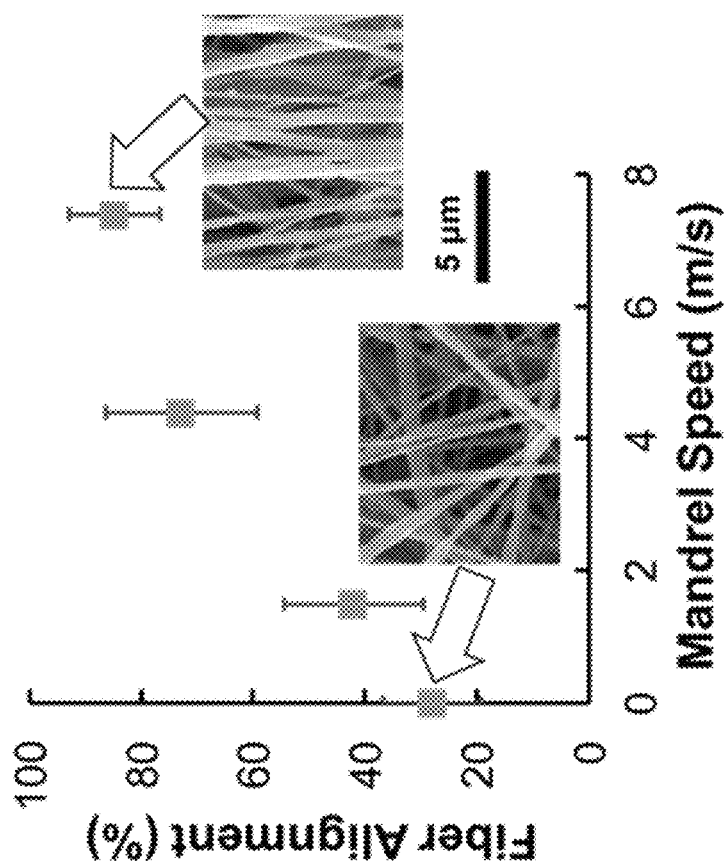
FIGS. 2A-2B show a process for electrospinning and the resulting fiber alignments. Detailed schematic of electrospinning setup using a rotating collection mandrel (FIG. 2A). Fiber alignment percentage as a function of mandrel rotating speed, with inset SEM images of fibers (FIG. 2B).
Figure 2A:
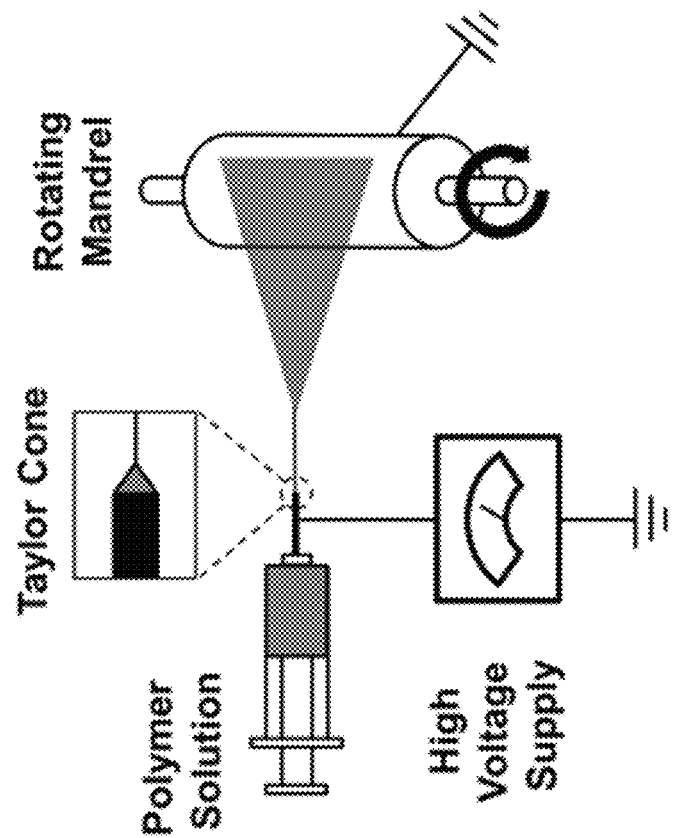
Figure 3C:
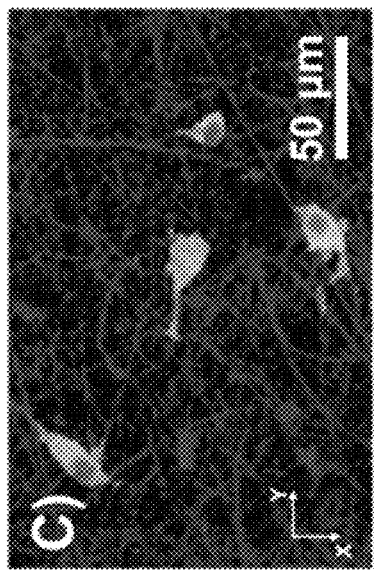
FIGS. 3A-3F show images of multicomponent electrospun fibers and biomolecule release. SEM (FIG. 3A) and fluorescent microscopy (FIG. 3B) of multicomponent fibrous scaffolds. Confocal microscopy shows cellular adhesion and infiltration into fibrous scaffolds (FIG. 3C & FIG. 3D). Burst release of collagenase from the PEO fiber component (FIG. 3E) and moderate, controlled release of PDGF from the HA fiber component (FIG. 3F).
Figure 3D:
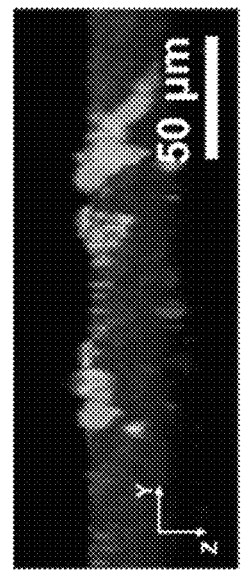
Figure 3B:
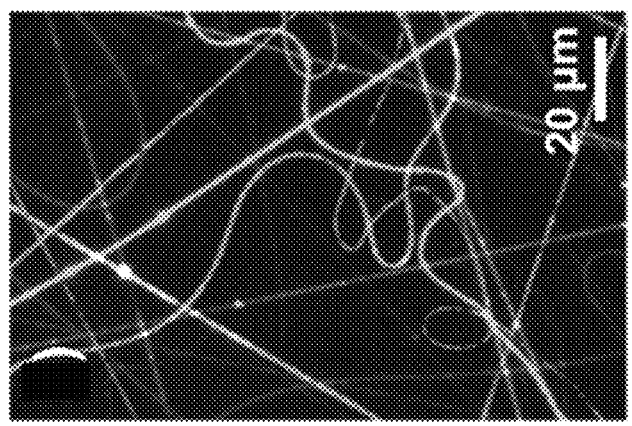
Figure 3A:
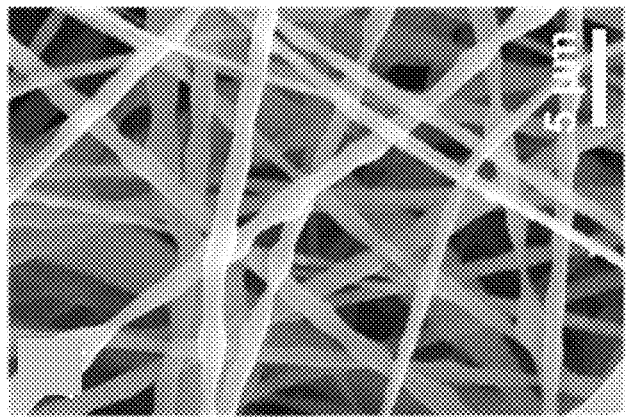
Figure 3F:
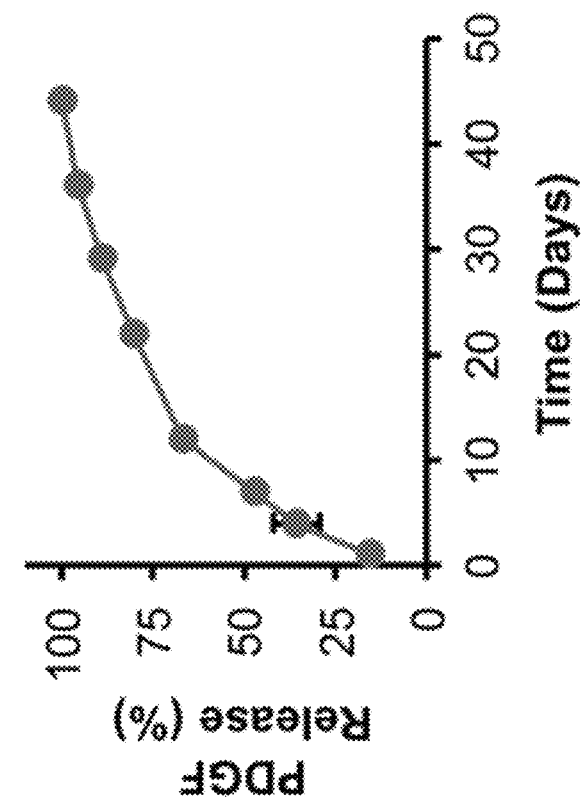
Figure 3E:
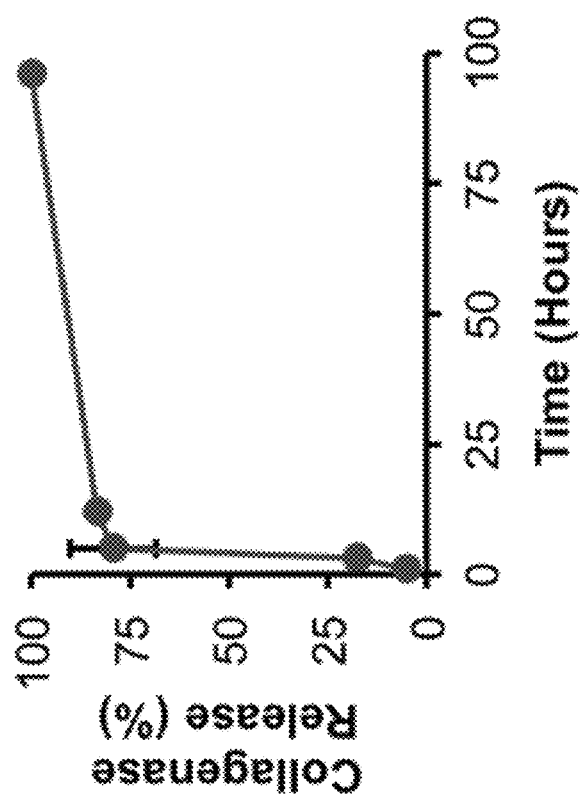

Methodology: HA will be functionalized with 30% norbornene functional groups according to established protocols. To promote cell adhesion, 2 mM RGD (GCGYGRGD-SPG (SEQ ID NO:1), italics indicate the cell adhesive domain) will be tethered to the norbornene-functionalized HA (NorHA). Electrospinning solutions containing 4 wt % NorHA (with RGD) and 2 wt % poly(ethylene oxide) (PEO, contributes to electrospinning stability) will be dissolved in water with a matrix metalloprotease (MMP)-degradable peptide (GCRDGPQG↓IWGQDRCG (SEQ ID NO: 3), down arrow indicating MMP cleavage site) to crosslink HA, 0.05 wt % Irgacure 2959 as the photoinitiator, and superparamagnetic $Fe_3O_4$ nanoparticles to induce alignment near magnets. The MMP-degradable peptide will be added in a 1:2 stoichiometric ratio of crosslinker to available norbornene groups in order reserve half of the norbornene groups for photoconjugation with bioactive peptides after electrospinning. Electrospinning will be performed onto a flat collection plate using the following approximate parameters: +24 kV applied voltage, 1.2 mL/hr polymer flow rate, and 16 cm spinneret to collector distance. To induce fiber alignment, a local magnetic field will be selectively applied using one or more flexible, permanent magnetic adhesive strips with poles alternating along the width or face of the adhesive adhered to the collector. The force of the magnetic field will be controlled using magnet size (thickness and width) and number, where magnetic field strength will be measured using a gaussmeter. The size of the aligned fiber component will be controlled by adding additional magnetic strips in "series" along the length of the rotating mandrel. Preliminary research using large bar magnets (FIG. 2) and polycaprolactone (PCL) as the electrospinning polymer indicates fiber alignment occurs in the presence of a magnetic field strength as low as 50 mT. Using this field strength as a starting point, we will optimize NorHA-based magnetically-assisted electrospinning using different magnets (magnet thickness: 0.03 to 0.125 in., magnet width: 0.01 to 0.5 in.) and nanoparticle concentrations in NorHA solution (0.1 to 5 wt % Fe3O4). After electrospinning, fibrous scaffolds will be exposed to 10 mW/cm2 of UV light for 5 minutes on each side in order to crosslink half the available norbornene groups within the HA fibers. Next, we will investigate the capacity of the system to spatially localize an osteogenic growth peptide (OGP, GCALKRQGRTLYGFGG (SEQ ID NO: 2); italics indicate bioactive osteogenic domain) signal by photopatterning using custom, CAD-designed photomask transparencies. NorHA fibers will be immersed in a solution containing 2 mM OGP and 0.05 wt % I2959, covered with a gradient photomask, and subjected to 10 mW/cm2 of UV light for 2 mins. Successful pattern formation will be verified visually by adding fluorophores onto the OGP peptide strands. Fibrous scaffold alignment will be quantified using scanning electron microscopy and chemical functionalization via x-ray spectroscopy as a function of length. Scaffolds will be tested via bulk tensile testing with local strain analysis via digital image correlation.

Example 9: Gradient Fibrous Materials as a "Patch" to Augment Rotator Cuff Repair in Vivo Fibrous scaffolds from Table 2 will be evaluated as a "patch" material to improve rotator cuff repair and healing in vivo. A supraspinatus tendon detachment and repair rat model will be used, where the fibrous patch will be placed over the supraspinatus tendon to bone interface during the repair process. Other researchers have investigated patch materials to augment rotator cuff repair; however, most of these materials were uniform and did not replicate the gradient nature of the tendon to bone interface.

Methodology: Fibrous scaffolds will be evaluated as patches to augment rotator cuff repair in vivo using a well-established supraspinatus tendon detachment and repair rat model. Briefly, animals will be anesthetized, an incision made over the scapulohumeral joint, and the deltoid muscle detached to access the supraspinatus tendon to bone junction. Next, the supraspinatus tendon will be detached sharply at its insertion to the humerus bone to create the tear. The sterile fibrous patch will be placed over the supraspinatus tendon and the tendon with patch will be reattached to the humerus and placed into its correct anatomical position. The deltoid muscle will be reattached and the incision closed. The surgery will be performed bilaterally in each shoulder joint, resulting in two samples per animal. All treatment groups in Table 2 will be investigated, including two additional control groups (healthy control with no injury and suture only control with no patch) for a total of nine treatment groups (n=12, six samples for histological and mechanical analysis each). After 8 weeks, animals will be euthanized and tissue dissected for analysis. Half of the tissue samples will be fixed, embedded, sectioned, and used for histological evaluation, including hematoxylin & eosin (H&E) and collagen staining (n=6). The other half of the tissue samples will be tested biomechanically to determine tissue modulus using an Instron 5943 as described previously.

TABLE 2

Electrospun Fibrous Scaffold Groups (7 total groups)

| Fibrous Scaffold Group | Bone Mimetic Region | Tendon Mimetic Region |
|---|---|---|
| Gradient in alignment | Unaligned HA | Aligned HA |
| Gradient in chemistry | Unaligned HA + 2 mM OGP | Unaligned HA |
| Gradient in alignment and chemistry | Unaligned HA + 2 mM OGP | Aligned HA |
| Homogeneous controls (no gradients) | Unaligned HA ± 2 mM OGP; Aligned HA ± 2 mM OGP (4 control groups) | |

Statistical Significance: Statistical significance will be assessed for all data using ANOVA with Tukey's post-hoc testing and a=0.05 (n=5). Animal numbers are based on a power analysis; assuming a 30% effect with 20% standard deviation and a power of 0.8, six samples are required to achieve statistical significance.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the invention are set out in the following numbered clause:

Clause 1. A fibrous material comprising a plurality of polymer fibers, wherein the plurality of fibers has a longitudinal alignment gradient of more than 70% aligned to less than 35% aligned.

Clause 2. The fibrous material of clause 1, wherein the fibrous material has a longitudinal composition gradient.

Clause 3. The fibrous material of clause 1 or 2, wherein the plurality of polymer fibers comprises a polymer selected from the group consisting of hyaluronic acid, polyethylene oxide, polyglycolic acid, polylactic acid, PLGA, polyolefin, polyacrylonitrile, polyurethane, polycarbonate, polycaprolactone, polyvinyl alcohol, cellulose, silk, polyaniline, polystyrene, chitosan, nylon, and combinations thereof.

Clause 4. The fibrous material of any of clauses 1-3, wherein the polymer fiber comprises a metal nanoparticle.

Clause 5. The fibrous material of any of clauses 1-3, wherein the polymer fiber does not comprise a metal nanoparticle.

Clause 6. The fibrous material of any of clauses 1-5, wherein the fibrous material comprises a biomolecule, a drug molecule or a combination thereof.

Clause 7. The fibrous material of any of clauses 1-6, wherein the polymer fiber comprises a biomolecule, a drug molecule or a combination thereof.

Clause 8. The fibrous material of clause 1 or 2, wherein the plurality of polymer fibers comprises a first fiber and a second fiber.

Clause 9. A fibrous material comprising a plurality of polymer fibers, the plurality of polymer fibers comprising: a first fiber; and a second fiber, wherein the fibrous material has a longitudinal composition gradient and the plurality of fibers has a longitudinal alignment gradient.

Clause 10. The fibrous material of any one of clauses 1-9, wherein the plurality of fibers has an average diameter of less than 5 µm.

Clause 11. The fibrous material of any one of clauses 8-10, wherein the first fiber is present at about 0.1% to about 95% by weight.

Clause 12. The fibrous material of any of clauses 8-11, wherein the second fiber is present at about 0.1% to about 95% by weight.

Clause 13. The fibrous material of any of clauses 8-12, wherein the first fiber and second fiber each individually comprise a polymer selected from the group consisting of hyaluronic acid, polyethylene oxide, polyglycolic acid, polylactic acid, PLGA, polyolefin, polyacrylonitrile, polyurethane, polycarbonate, polycaprolactone, polyvinyl alcohol, cellulose, silk, polyaniline, polystyrene, chitosan, nylon, and combinations thereof.

Clause 14. The fibrous material of any of clauses 8-13, further comprising a third fiber.

Clause 15. The fibrous material of any of clauses 8-14, wherein at least one of the fibers comprises a metal nanoparticle.

Clause 16. The fibrous material of any of clauses 8-15, wherein the first fiber, the second fiber, the third fiber, or a combination thereof, comprises the metal nanoparticle.

Clause 17. The fibrous material of any of clauses 8-15, wherein at least one of the fibers does not comprise a metal nanoparticle.

Clause 18. The fibrous material of any of clauses 8-17, wherein the longitudinal composition gradient comprises a biomolecule, a drug molecule or a combination thereof.

Clause 19. The fibrous material of any of clauses 8-18, wherein at least one of the fibers individually comprises a biomolecule, a drug molecule or a combination thereof.

Clause 20. The fibrous material of any of clauses 8-19, wherein the first fiber, the second fiber, the third fiber, or a combination thereof, comprises a biomolecule, a drug molecule or a combination thereof.

Clause 21. A method of preparing a fibrous material comprising a plurality of polymer fibers, the method comprising: electrospinning a polymer fiber onto a collector having a first portion and a second portion to provide a fibrous material of any of clauses 1-7, wherein at least one portion of the collector comprises a magnetic field.

Clause 22. A method of preparing a fibrous material comprising a plurality of polymer fibers, the method comprising: electrospinning a first fiber and a second fiber onto a collector having a first portion and a second portion to provide a fibrous material of any of clauses 8-20, wherein at least one portion of the collector comprises a magnetic field.

Clause 23. The method of clause 22, wherein at least one of the fibers comprises a metal nanoparticle.

Clause 24. The method of clause 22 or 23, wherein the first fiber, the second fiber, or a combination thereof, comprises a metal nanoparticle Clause 25. The method of any of clauses 21-24, wherein the magnetic field is created by at least one magnet.

Clause 26. The method of any of clauses 21-25, wherein the applied magnetic field is greater than or equal to 1 mT.

Clause 27. The method of any of clauses 22-26, wherein electrospinning the first fiber and the second fiber are done simultaneously or sequentially.

Clause 28. The method of any of clauses 22-27, wherein the first fiber is electrospun onto the first portion of the collector and the second fiber is electrospun onto the second portion of the collector.

Clause 29. The method of any of clauses 22-28, further comprising electrospinning a third fiber onto the collector.

Clause 30. The method of clause 21, further comprising photoconjugating a biomolecule to the fibrous material.

Clause 31. The method of clause 30, wherein the biomolecule is photoconjugated to at least one polymer fiber.

Clause 32. The method of clause 30 or 31, wherein the biomolecule is photoconjugated to the fibrous material after electrospinning.

Clause 33. The method of any one of clauses 30-32, wherein the biomolecule is photoconjugated to the polymer fiber by photo treating the fibrous material or by photo treating the polymer fiber.

Clause 34. The method of any of clauses 22-29, further comprising photoconjugating a biomolecule to the fibrous material.

Clause 35. The method of clause 34, wherein the biomolecule is photoconjugated to at least one of the fibers.

Clause 36. The method of clause 34 or 35, wherein the biomolecule is photoconjugated to the first fiber, the second fiber, the third fiber, or a combination thereof.

Clause 37. The method of any one of clauses 34-36, wherein the biomolecule is photoconjugated to the fiber by photo treating the fibrous material or by photo treating the first fiber, the second fiber, the third fiber, or a combination thereof.

Clause 38. The method of clause 30 or 34, wherein the biomolecule is photoconjugated to the fibrous material using UV light or visible light.

Clause 39. The method of clause 33 or 37, wherein the biomolecule is photoconjugated to the fiber using UV light or visible light.

Clause 40. The method of clause 38 or 39, further comprising using at least one photo-opaque mask to create at least one longitudinal gradient in the biomolecule conjugation.

Clause 41. A method of treating organ or tissue damage in a subject, the method comprising introducing a fibrous material of any one of clause 1-20 into a subject in need thereof at or near the organ or tissue.

Clause 42. The method of clause 41, wherein the organ or tissue is musculoskeletal tissue.

Clause 43. The method of clause 41 and 42, wherein the organ or tissue is the rotator cuff.

Clause 44. The method of clause 41-43, wherein the fibrous material is applied as a patch and sutured onto the injured rotator cuff. Various features and advantages of the invention are set forth in the following claims.

What is claimed is:

1. A method of preparing a fibrous material comprising a plurality of polymer fibers, the method comprising:
   generating a magnetic field on a first portion of a collector;
   electrospinning a polymer fiber onto the first portion of the collector and onto a second portion of the collector to provide a fibrous material, such that fibers in the first portion are generally aligned and fibers in the second portion are generally not aligned, the fibrous material comprising a plurality of polymer fibers, wherein the plurality of fibers has a longitudinal alignment along the collector axis with a gradient of more than 70% aligned to less than 35% aligned.

2. The method of claim 1, wherein the magnetic field is created by at least one magnet.

3. The method of claim 1, wherein the applied magnetic field is greater than or equal to 1 mT.

4. The method of claim 1, wherein a first fiber and a second fiber are electrospun onto the collector.

5. The method of claim 4, wherein the first fiber is electrospun onto the first portion of the collector and the second fiber is electrospun onto the second portion of the collector.

6. The method of claim 5, further comprising electrospinning a third fiber onto the collector.

7. The method of claim 1, further comprising photoconjugating a biomolecule to the fibrous material.

8. The method of claim 7, wherein the biomolecule is photoconjugated to the fibrous material using UV light or visible light.

9. The method of claim 7, further comprising using at least one photo-opaque mask to create at least one longitudinal gradient in the biomolecule conjugation.

\* \* \* \* \*